US009050195B2

(12) United States Patent
DeFalco et al.

(10) Patent No.: US 9,050,195 B2
(45) Date of Patent: *Jun. 9, 2015

(54) EXPANDABLE SPINAL IMPLANT DEVICE

(71) Applicant: EBI, LLC, Parsippany, NJ (US)

(72) Inventors: Anthony C. DeFalco, Andover, NJ (US); Rawley Stanhope, Boonton, NJ (US)

(73) Assignee: EBI, LLC, Parsippany, NJ (US)

( * ) Notice: Subject to any disclaimer, the term of this patent is extended or adjusted under 35 U.S.C. 154(b) by 83 days.

This patent is subject to a terminal disclaimer.

(21) Appl. No.: 13/761,265

(22) Filed: Feb. 7, 2013

(65) Prior Publication Data

US 2013/0150971 A1     Jun. 13, 2013

Related U.S. Application Data

(62) Division of application No. 13/005,021, filed on Jan. 12, 2011, now Pat. No. 8,377,140.

(51) Int. Cl.
*A61F 2/44*     (2006.01)
*A61F 2/46*     (2006.01)
(Continued)

(52) U.S. Cl.
CPC ... *A61F 2/44* (2013.01); *A61F 2/28* (2013.01); *A61F 2/4611* (2013.01); *A61F 2002/2817* (2013.01); *A61F 2002/3041* (2013.01); *A61F 2002/30411* (2013.01); *A61F 2002/30495* (2013.01); *A61F 2002/30523* (2013.01); *A61F 2002/3055* (2013.01); *A61F 2002/30601* (2013.01); *A61F 2002/30841* (2013.01); *A61F 2002/4475* (2013.01); *A61F 2220/0025* (2013.01); *A61F 2310/00023* (2013.01)

(58) Field of Classification Search
USPC .......................................... 623/17.11–17.16
See application file for complete search history.

(56) References Cited

U.S. PATENT DOCUMENTS

| 4,636,217 A | 1/1987 | Ogilvie et al. |
| 5,336,223 A | 8/1994 | Rogers |

(Continued)

FOREIGN PATENT DOCUMENTS

| EP | 1925272 A1 | 5/2008 |
| WO | 200510112834 A2 | 12/2005 |

OTHER PUBLICATIONS

European Search Report and Written Opinion dated May 18, 2012 for European Patent Application No. 12150973.1.
(Continued)

*Primary Examiner* — Jan Christopher Merene
(74) *Attorney, Agent, or Firm* — Harness, Dickey

(57) ABSTRACT

An expandable spinal implant device for supporting vertebral bodies can include first and second body members and first and second expansion mechanisms. The body members can each have a first end positionable toward one of the vertebral bodies and can each define a hollow interior. The expansion mechanisms can be spaced apart from each other and can include a first drive shaft and a second drive shaft, respectively. The first and second drive shafts can each have a gear member fixedly coupled thereto. Each drive shaft can be threadably engaged at a first side to the first body member and at a second side to the second body member. The expansion mechanisms can be operable to effect axial displacement of the first body member relative to the second body member by rotationally driving the gear members of the first and second drive shafts.

19 Claims, 15 Drawing Sheets

(51) Int. Cl.
  *A61F 2/28* (2006.01)
  *A61F 2/30* (2006.01)

(56) References Cited

U.S. PATENT DOCUMENTS

| | | | |
|---|---|---|---|
| 5,458,641 A | 10/1995 | Ramirez Jimenez | |
| 5,480,442 A * | 1/1996 | Bertagnoli | 623/17.14 |
| 5,571,192 A | 11/1996 | Schonhoffer | |
| 5,683,399 A | 11/1997 | Jones | |
| 5,697,889 A | 12/1997 | Slotman et al. | |
| 5,702,451 A | 12/1997 | Biedermann et al. | |
| 5,702,453 A | 12/1997 | Rabbe et al. | |
| 5,702,455 A | 12/1997 | Saggar | |
| 5,776,198 A | 7/1998 | Rabbe et al. | |
| 5,782,830 A | 7/1998 | Farris | |
| 5,827,328 A | 10/1998 | Buttermann | |
| 5,885,299 A | 3/1999 | Winslow et al. | |
| 5,916,267 A | 6/1999 | Tienboon | |
| 5,989,290 A | 11/1999 | Biedermann et al. | |
| 6,015,436 A | 1/2000 | Schonhoffer | |
| 6,066,174 A | 5/2000 | Farris | |
| 6,086,613 A | 7/2000 | Camino et al. | |
| 6,126,660 A | 10/2000 | Dietz | |
| 6,159,215 A | 12/2000 | Urbahns et al. | |
| 6,176,881 B1 | 1/2001 | Schar et al. | |
| 6,190,414 B1 | 2/2001 | Young et al. | |
| 6,193,755 B1 | 2/2001 | Metz-Stavenhagen et al. | |
| 6,193,756 B1 | 2/2001 | Studer et al. | |
| 6,200,348 B1 | 3/2001 | Biedermann et al. | |
| 6,344,057 B1 | 2/2002 | Rabbe et al. | |
| 6,454,806 B1 | 9/2002 | Cohen et al. | |
| 6,524,341 B2 | 2/2003 | Lang et al. | |
| 6,616,695 B1 | 9/2003 | Crozet et al. | |
| 6,752,832 B2 | 6/2004 | Neumann | |
| 6,776,798 B2 | 8/2004 | Camino et al. | |
| 6,808,538 B2 | 10/2004 | Paponneau | |
| 6,866,682 B1 | 3/2005 | An et al. | |
| 6,902,579 B2 | 6/2005 | Harms et al. | |
| 6,929,662 B1 | 8/2005 | Messerli et al. | |
| 7,018,415 B1 | 3/2006 | McKay | |
| 7,056,343 B2 | 6/2006 | Schafer et al. | |
| 7,118,579 B2 | 10/2006 | Michelson | |
| 7,156,874 B2 | 1/2007 | Paponneau et al. | |
| 7,179,261 B2 | 2/2007 | Sicvol et al. | |
| 7,226,453 B2 | 6/2007 | Chao et al. | |
| 7,384,431 B2 | 6/2008 | Berry | |
| 7,544,208 B1 | 6/2009 | Mueller et al. | |
| 7,547,325 B2 | 6/2009 | Biedermann et al. | |
| 7,563,281 B2 | 7/2009 | Sears et al. | |
| 7,575,581 B2 | 8/2009 | Lovell | |
| 7,575,601 B2 | 8/2009 | Dickson | |
| 7,608,078 B2 | 10/2009 | Berry | |
| 7,628,815 B2 | 12/2009 | Baumgartner et al. | |
| 7,641,693 B2 | 1/2010 | Gutlin et al. | |
| 8,070,813 B2 | 12/2011 | Grotz et al. | |
| 8,241,362 B2 * | 8/2012 | Voorhies | 623/17.16 |
| 8,409,283 B2 * | 4/2013 | Drochner et al. | 623/17.11 |
| 2002/0099443 A1 | 7/2002 | Messerli et al. | |
| 2004/0153160 A1 | 8/2004 | Carrasco | |
| 2004/0186569 A1 | 9/2004 | Berry | |
| 2005/0060034 A1 | 3/2005 | Berry et al. | |
| 2005/0107878 A1 | 5/2005 | Conchy | |
| 2005/0240268 A1 | 10/2005 | Messerli et al. | |
| 2006/0058877 A1 | 3/2006 | Gutlin et al. | |
| 2006/0069436 A1 | 3/2006 | Sutton et al. | |
| 2006/0084975 A1 | 4/2006 | Berry | |
| 2006/0100710 A1 | 5/2006 | Gutlin et al. | |
| 2006/0136062 A1 | 6/2006 | DiNello et al. | |
| 2006/0142863 A1 | 6/2006 | Fraser et al. | |
| 2006/0149385 A1 | 7/2006 | McKay | |
| 2006/0200244 A1 | 9/2006 | Assaker | |
| 2006/0241762 A1 | 10/2006 | Kraus | |
| 2006/0241770 A1 | 10/2006 | Rhoda et al. | |
| 2006/0293755 A1 | 12/2006 | Lindner et al. | |
| 2007/0191954 A1 | 8/2007 | Hansell et al. | |
| 2007/0198089 A1 | 8/2007 | Moskowitz et al. | |
| 2007/0250171 A1 | 10/2007 | Bonin | |
| 2007/0255407 A1 | 11/2007 | Castleman et al. | |
| 2007/0255408 A1 | 11/2007 | Castleman et al. | |
| 2007/0255409 A1 | 11/2007 | Dickson et al. | |
| 2007/0255410 A1 | 11/2007 | Dickson et al. | |
| 2007/0255415 A1 | 11/2007 | Edie et al. | |
| 2007/0255421 A1 | 11/2007 | Dickson | |
| 2008/0015704 A1 | 1/2008 | Gradl et al. | |
| 2008/0161933 A1 | 7/2008 | Grotz et al. | |
| 2008/0167720 A1 | 7/2008 | Melkent | |
| 2008/0177387 A1 | 7/2008 | Parimore et al. | |
| 2008/0243254 A1 | 10/2008 | Butler | |
| 2009/0112217 A1 | 4/2009 | Hester | |
| 2009/0112324 A1 | 4/2009 | Refai et al. | |
| 2009/0112325 A1 | 4/2009 | Refai et al. | |
| 2009/0125062 A1 | 5/2009 | Arnin | |
| 2009/0132053 A1 | 5/2009 | Sears et al. | |
| 2009/0138083 A1 | 5/2009 | Biyani | |
| 2009/0138089 A1 | 5/2009 | Doubler et al. | |
| 2009/0164017 A1 | 6/2009 | Sommerich et al. | |
| 2009/0164019 A1 | 6/2009 | Hsu et al. | |
| 2009/0210061 A1 | 8/2009 | Sledge | |
| 2010/0016968 A1 | 1/2010 | Moore | |
| 2010/0016969 A1 | 1/2010 | Richter et al. | |
| 2010/0016970 A1 | 1/2010 | Kapitan et al. | |
| 2010/0016971 A1 | 1/2010 | Berry | |
| 2010/0016972 A1 | 1/2010 | Jansen et al. | |
| 2010/0016973 A1 | 1/2010 | de Villiers et al. | |
| 2010/0016974 A1 | 1/2010 | Janowski et al. | |
| 2010/0324687 A1 * | 12/2010 | Melkent et al. | 623/17.16 |
| 2011/0160861 A1 | 6/2011 | Jimenez et al. | |
| 2011/0172716 A1 | 7/2011 | Glerum | |

OTHER PUBLICATIONS

U.S. Office Action regarding U.S. Appl. No. 13/005,021 dated Jul. 17, 2012.
Stryker; "VLIFT® System Overview" brochure; Copyright © 2006 Stryker.
Ulrich Medical, "SpineSource VBR™ vertebral replacement body" brochure; WS 2230/10-04.
Ulrich Medical, "Obelisc System" brochure; WS 2913 Rev 01/02-07.
Synthes; "SynMesh System" brochure; © Synthes, (USA) 2000; GP1487-A 4/-00 J3079.
Synthes; "SynMesh System Technique Guide"; © Synthes, (USA) 2002; GP2170-B 8104 J4124-B.
Stryker, "Vertebral Body Support System (VBOSS)" product information; www.stryker.com/en-us/products.htm.
Alphatec; "Tecorp-C—Versatile cervical vertebral body replacement system" product information; www.alphatecspine.com.
Alphatec; "TECORP: Corporectomy VBR system" product information; www.alphatecspine.com.
Synthes; "ECD—Expandable Corpectomy Device. Continuously Expandable Vertebral Body Replacement for Tumour Cases" Technique Guide; © Synthes 2006.
B Braun; "Aesculap Spine Hydrolift Next Generation Vertebral Body Replacement" Brochure No. 029302; www.aesculap.de.

* cited by examiner

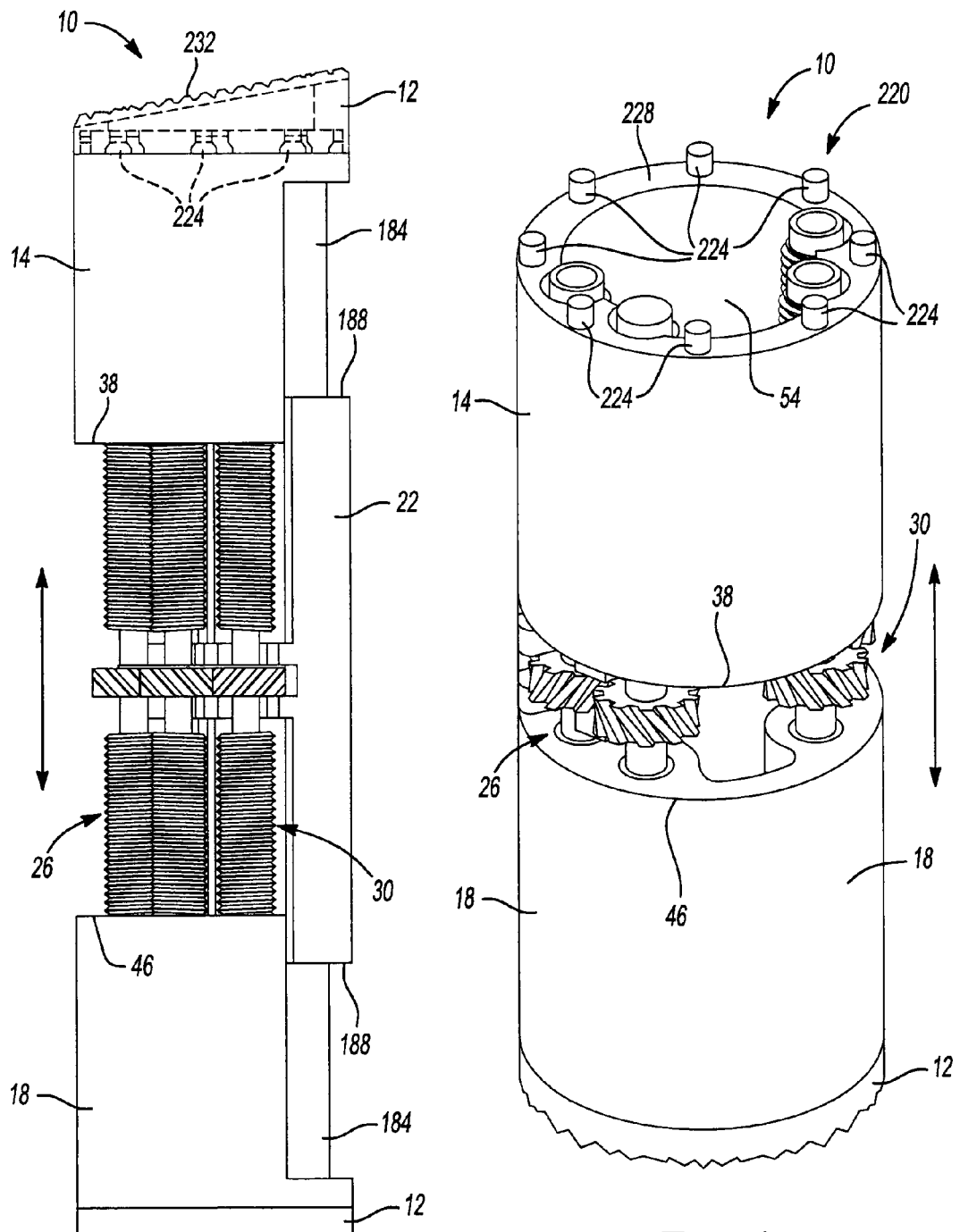

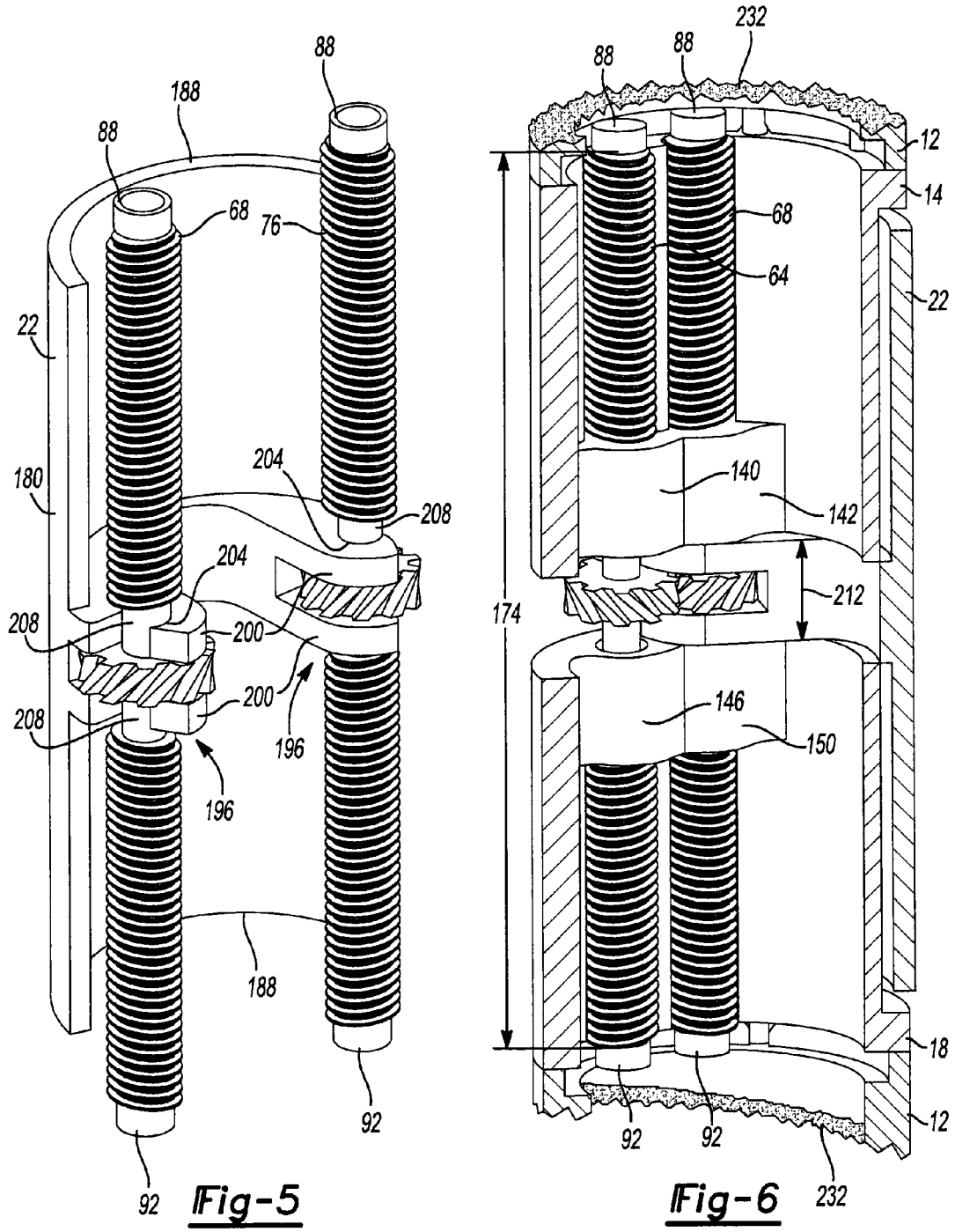

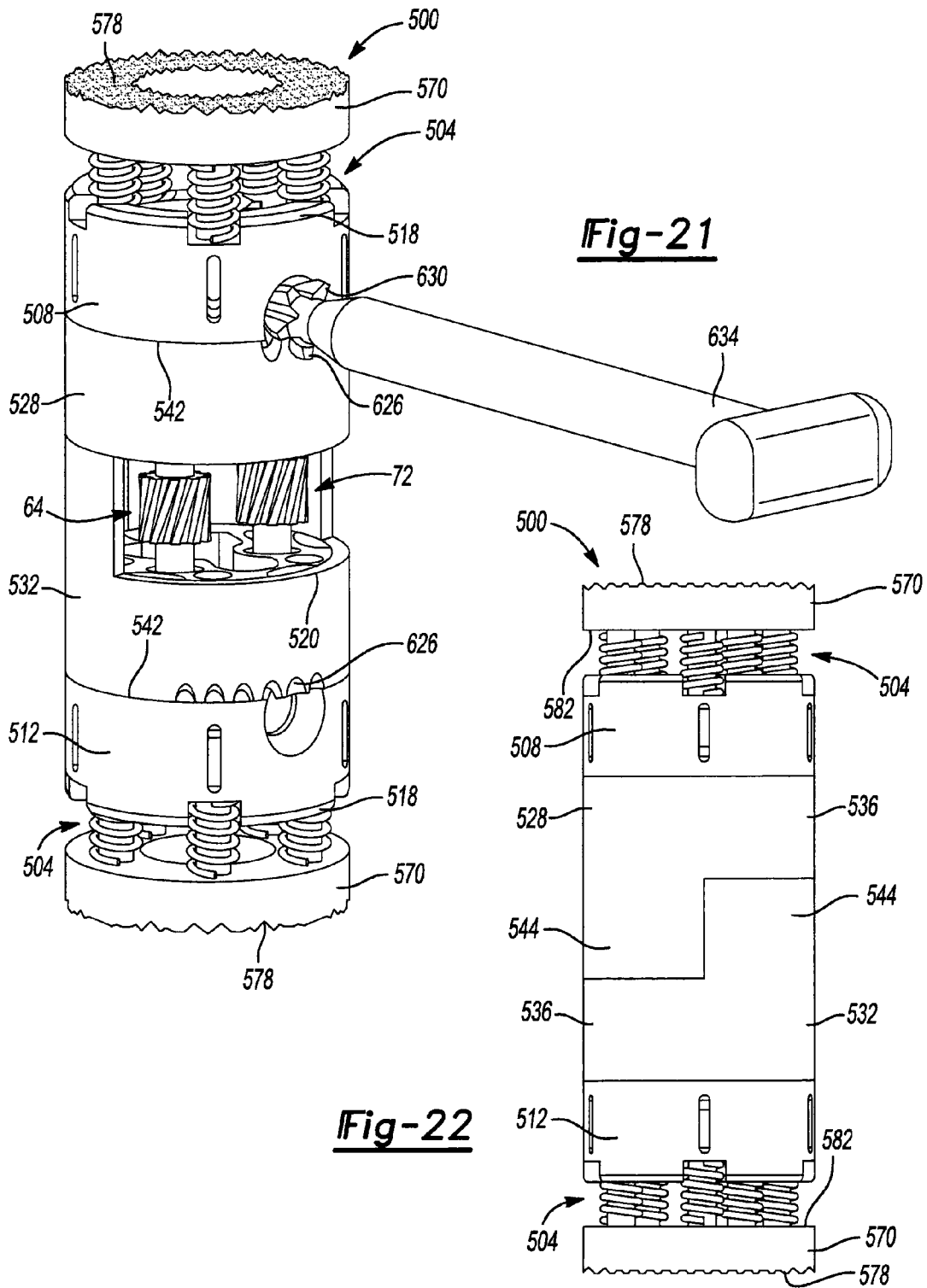

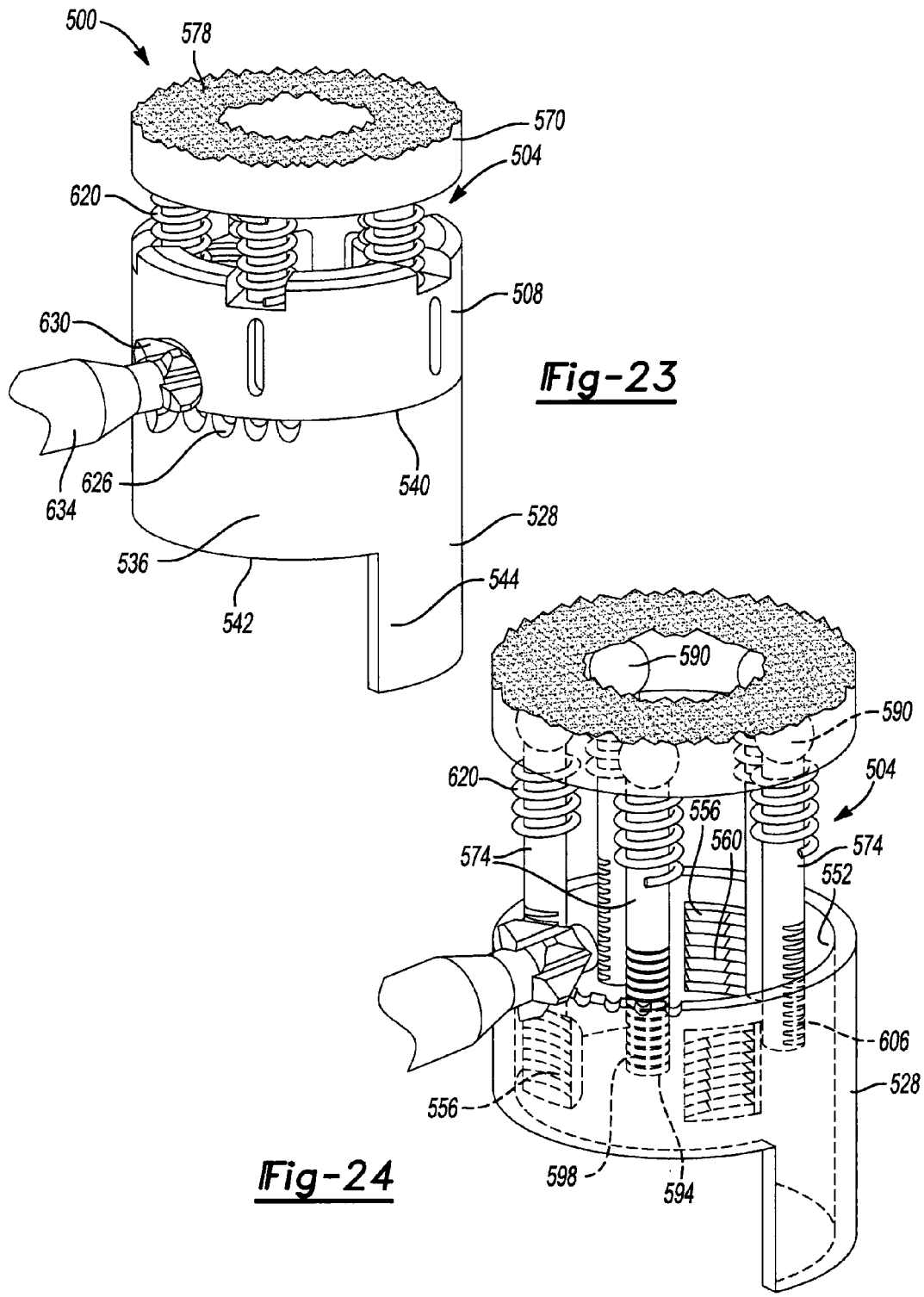

EXPANDABLE SPINAL IMPLANT DEVICE

CROSS-REFERENCE TO RELATED APPLICATIONS

This application is a continuation of U.S. patent application Ser. No. 13/005,021, filed on Jan. 12, 2011, now U.S. Pat. No. 8,377,140, issued on Feb. 19, 2013. The disclosure of the above referenced application is incorporated herein by reference.

FIELD

The present disclosure relates generally to an expandable spinal implant device for supporting vertebral bodies.

INTRODUCTION

Spinal implants can be used to support and/or replace one or more vertebrae, or a portion of the vertebrae from the human spine in response to various pathologic conditions in the spine. These conditions can include, for example, infectious, degenerative, and oncologic conditions. Removal or excision of an anterior portion of the vertebra, or vertebral body, may be referred to as a corpectomy procedure. Various known vertebral body replacement devices can be positioned between the remaining vertebrae after the corpectomy procedure to provide support for the spine. These devices can be adjustable or can be available in a variety of fixed length sizes, where an appropriate size is selected prior to implantation. Adjustable implants can be advantageous because they can allow for a smaller incision when positioning the implant, as well as may assist in restoring proper loading to the spine.

While spinal implant devices have generally worked for their intended purpose, there remains a need for continuous improvement in the relevant art.

SUMMARY

This section provides a general summary of the disclosure, and is not a comprehensive disclosure of its full scope or all of its features.

In accordance with one aspect, the present teachings provide an expandable spinal implant device for supporting vertebral bodies. The device can include a first body member and a second body member that each have first and second ends and define a hollow interior, where the first ends of each body member can be positionable toward a respective one of the vertebral bodies. A first expansion mechanism can include a first pair of drive shafts and a second expansion mechanism can be spaced apart from the first expansion mechanism and can include a second pair of drive shafts. The respective drive shafts of each pair of drive shafts can have a gear member rotationally coupling the respective drive shafts to each other, where each pair of drive shafts can be threadably engaged at a first side to the first body member and at a second side to the second body member. The first and second expansion mechanisms can be operable to effect axial displacement of the first body member relative to the second body member by rotationally driving one of the gear members of each pair of drive shafts.

In accordance with another aspect, the present teachings provide an expandable spinal implant device for supporting vertebral bodies. The device can include a first body member and a second body member that each have first and second ends and define a hollow interior, where the first ends of each body member can be positionable toward a respective one of the vertebral bodies. A first expansion mechanism can have a first pair of drive shafts and a second expansion mechanism can be spaced apart from the first expansion mechanism and can have a second pair of drive shafts. The respective drive shafts of each pair of drive shafts can have a central gear member rotationally coupling the respective shafts to each other, where each pair of drive shafts can be threadably engaged at a first side to the first body member and at a second side to the second body member. A central body member can be coupled to at least one shaft of the first and second expansion mechanisms and can be configured to slidably engage an exterior surface of the first and second body members. A first endplate and a second endplate can each have a bone engagement portion and a device engaging portion configured to facilitate coupling each endplate to the first end of a respective body member in one of a plurality of circumferential orientations relative to the respective body member. The first and second expansion mechanisms can be operable to effect axial displacement of the first body member relative to the second body member by rotationally driving one of the gear members of each pair of drive shafts.

In accordance with yet another aspect, the present teachings provide an expandable spinal implant device for supporting vertebral bodies. The device can include a first endplate, a second endplate and a body member defining a hollow interior and having first and second ends. The first and second endplates can each have a bone engagement portion and a device engaging portion. The device engaging portion of the first endplate can have a coupling arrangement configured to facilitate coupling the first endplate to the second end of the body member in one of a plurality of circumferential orientations relative to the body member. A first and second pair of drive shafts can be spaced apart from each other, where the drive shafts of each pair of drive shafts can have a gear member at a first end and a threaded portion extending to a second opposite end. The gear members can rotationally couple the respective drive shafts of each pair of drive shafts together, and the threaded portions of each pair of drive shafts can threadably engage the body member. The first end of each pair of drive shafts can be rotationally coupled to the device engaging side of the second endplate. The first and second expansion mechanisms can be operable to effect axial displacement of the body member relative to the second endplate by simultaneously driving one of the gear members of each pair of drive shafts.

In accordance with still another aspect, the present teachings provide an expandable spinal implant device for supporting vertebral bodies. The device can include a first body member and a second body member each having first and second ends, where the first ends of each body member can be positionable toward a respective one of the vertebral bodies. A first drive shaft and a second drive shaft can each include a drive gear and can each be threadably engaged at a first side to the first body member and at a second side to the second body member. First and second intermediate body members can be rotationally coupled to the respective first and second body members about the second ends thereof. A first endplate assembly and a second endplate assembly can each have a bone engagement member and a plurality of axially extending members pivotally coupled to the bone engaging member at a first end and slidably coupled to one of the respective first and second body members at a second end. Each of the plurality of posts can be individually adjustable relative to the respective first or second body members to position the bone engagement member in one of a plurality of positions relative to the respective first or second body members. The first and second expansion mechanisms can be operable to effect axial displacement of the first body member relative to the second body member by rotationally driving the gear member of each drive shaft.

Additional advantages and further areas of applicability will become apparent from the following description and appended claims. The description and specific examples in this summary are intended for purposes of illustration only and are not intended to limit the scope of the present teachings.

DRAWINGS

The drawings described herein are for illustrative purposes only and are not intended to limit the scope of the present teachings in any way.

FIG. 3 is a side view of the expandable spinal implant device of FIG. 1 in an expanded state;

FIG. 4 is a perspective view of the expandable spinal implant device of FIG. 1 with an upper or superior endplate removed for purposes of illustration;

FIG. 5 is a partial perspective view of the expandable spinal implant device of FIG. 1;

FIG. 6 is a cross-sectional view of the expandable spinal implant device of FIG. 1 along line 6-6;

FIG. 21 is a perspective view of an exemplary expandable spinal implant device carrying articulating endplates and shown associated with an exemplary instrument according to the principles of the present teachings;

FIG. 22 is a side view of the expandable device of FIG. 21;

FIG. 23 is a partial perspective view of the expandable spinal implant device of FIG. 21 with an endplate in a non-expanded state;

FIG. 24 is a partial perspective view of the expandable spinal implant device of FIG. 21 with an endplate in an expanded state;

DESCRIPTION OF VARIOUS ASPECTS

Figure 1:
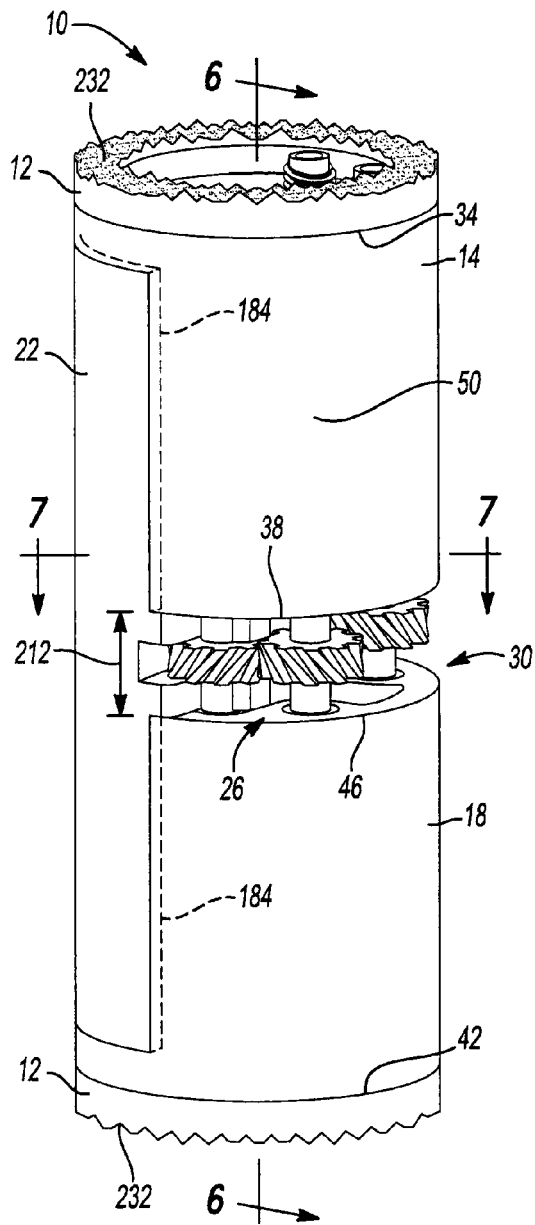
FIG. 1 is a perspective view of an exemplary expandable spinal implant device carrying modular endplates according to the principles of the present teachings.

The following description is merely exemplary in nature and is not intended to limit the present teachings, application, or uses. It should be understood that throughout the several views of the drawings, corresponding reference numerals indicate like or corresponding components and features, with the various elements within each view being drawn to scale. Although the following description is related generally to an expandable spinal implant device for use in a spinal column to support vertebral bodies, it will be understood that the devices and methods discussed herein can also be applicable to other appropriate surgical procedures involving the spine or other long bones of the anatomy. Therefore, it will be understood that the following discussions are not intended to limit the scope of the present teachings and claims herein.

Throughout the description, example embodiments are provided so that this disclosure will be thorough, and will fully convey the scope to those who are skilled in the art. Numerous specific details are set forth such as examples of specific components, devices, and methods, to provide a thorough understanding of the aspects of the present disclosure. It will be apparent to those skilled in the art that specific details need not be employed, that the examples may be embodied in many different forms and that neither should be construed to limit the scope of the disclosure. In some examples, well-known processes, well-known device structures, and well-known technologies are not discussed in detail.

With reference to FIGS. 1-7, an expandable spinal implant device 10 is shown carrying modular endplates 12 according to one aspect of the present teachings. The device 10 can include a first or superior body member 14, a second or inferior body member 18, a central body member or backstop 22 and a pair of expansion mechanisms 26, 30 rotatably coupled to the first and second body members 14, 18. The first body member 14 can include a first end 34 and a second end 38 and the second body member 18 can similarly include a first end 42 and a second end 46. The first and second body members 14, 18 can each include a generally cylindrical shape 50 and can each define a hollow interior 54 extending therethrough. In one exemplary configuration, the first and second body members 14, 18 can have a solid construction without any apertures or the like being formed therethrough.

The first and second body members 14, 18, as well as the central body member 22, can be coaxial about a longitudinal axis 60 of the device 10. It should be appreciated that while the first and second body members 14, 18 are shown having a generally cylindrical shape with the same diameters, other shapes can be used including, for example, oval, square and rectangular shapes in cross-section. The first and second body members 14, 18 can be formed from a suitable biocompatible polymeric material such as polyetheretherketone (PEEK) that is either solid or porous. In one exemplary configuration, the first and second body members 14, 18 can have the same longitudinal length. Alternatively, the first and second body members 14, 18 can have different lengths.

The expansion mechanism 26 can include a pair of drive shafts 64, 68 and the expansion mechanism 30 can similarly include a pair of drive shafts 72, 76. The expansion mechanisms 26, 30, via the associated drive shafts, can be operable to expand and contract the body members 14, 18 of device 10, as will be discussed below. Briefly, however, one drive shaft or each pair of drive shafts can be rotated or driven by an instrument to effect axial expansion and contraction of the first and second body members 14, 18 relative to each other. For example, the instrument can be used to expand the first and second body member 14, 18 so that the spinal implant device 10 engages and supports the opposed vertebral bodies.

Figure 2:
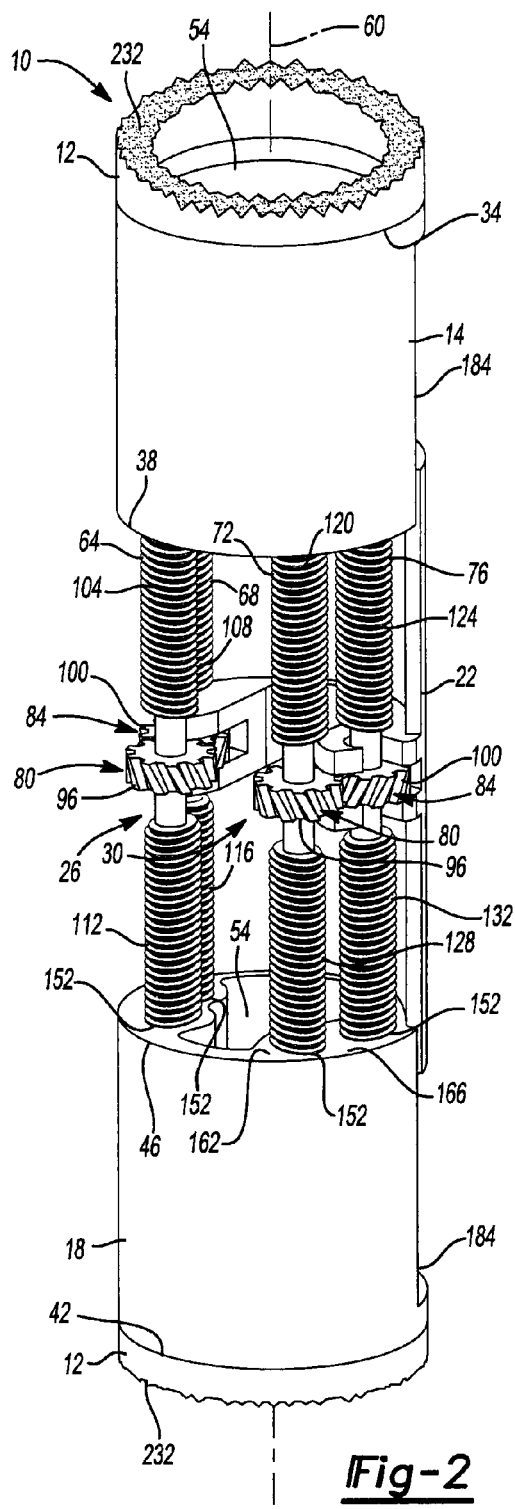
FIG. 2 is a perspective view of the expandable spinal implant device of FIG. 1 in an expanded state.

The drive shafts 64, 68 and 72, 76 can each include respective gear members 80, 84 generally centrally positioned between first and second ends 88, 92 of the drive shafts, as generally shown in FIG. 2 with reference to FIG. 6. The gear members 80, 84 can each include opposite gear configurations 96, 100 intermeshing with each other such that rotation of gear member 80 can cause corresponding rotation of gear member 84. Gear members 80, 84 can be fixedly attached to their respective shafts such that rotation of the gear members causes corresponding rotation of the associated drive shaft. Each pair of gear members 80, 84 can include opposite gear angles to facilitate the intermeshing operation of the gear members discussed above. In one exemplary configuration, gear member 80 can include a gear configuration 96 having a 45 degree helical gear angle and gear member 84 can include a gear configuration 100 having an opposite helical gear angle of −45 degrees, as shown for example in FIGS. 1 and 2. It should be appreciated, however, that various other gear angles and patterns can be used for intermeshing operation of gear members 80, 84.

The drive shafts 64, 68 of expansion mechanism 26 can include respective upper threaded portions 104, 108 between gear members 80, 84 and the first ends 88, and lower threaded portions 112 and 116 between the gear members and the opposite second ends 92, as shown for example in FIGS. 2-3 and 6. In a similar manner, drive shafts 72, 76 can include upper threaded portions 120, 124 between gear members 80, 84 and the first ends 88, and lower threaded portions 128 and 132 between the gear members and the opposite second ends 92.

Figure 7:
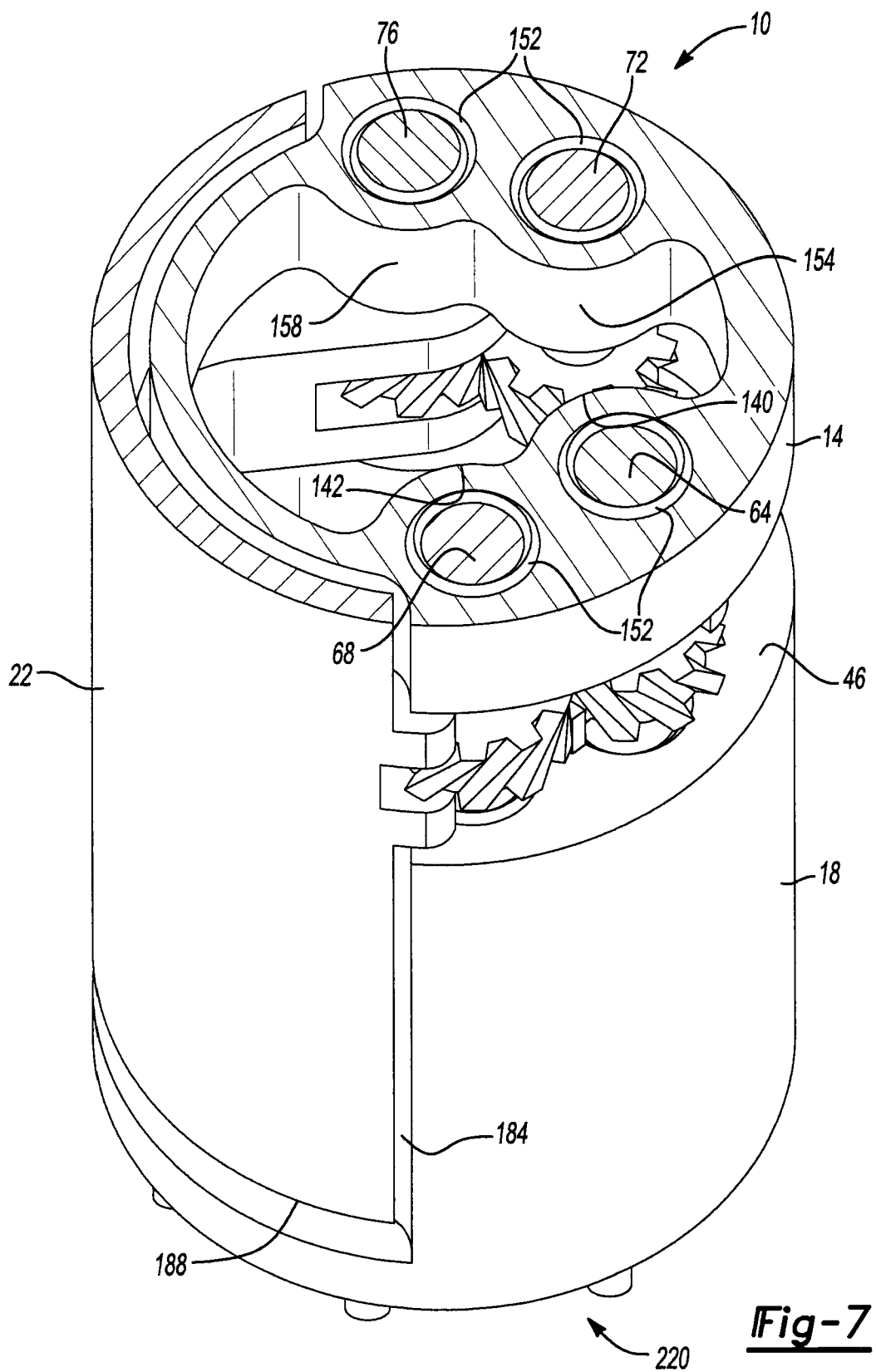
FIG. 7 is a cross-sectional view of the expandable spinal implant device of FIG. 1 along line 7-7.

The first and second body members 14, 18 can each include attachment portions disposed about a sidewall 136 that can threadably receive the drive shafts 64, 68 and 72, 76. With particular reference to the FIGS. 2, 6 and 7, the drive shafts 64, 68 are shown threadably coupled to respective attachment portions 140, 142 in body member 14 and attachment portions 146, 150 in body member 18. In addition, the drive shafts 72, 76 are shown threadably coupled to attachment portions 154, 158 in body member 14 and attachment portions 162, 166 in body member 18, as shown in FIGS. 2 and 7.

In this regard, each pair of drive shafts 64, 68 and 72, 76 can be positioned relative to the sidewall 136 in attachment portions 140-166 such that the drive shafts are not coaxial with the body members 14, 18. The drive shafts 64, 68 and 72, 76 can rotationally fix the body members 14, 18 relative to each other. Each of the attachment portions 140-166 can include internal threads 152 complementary to the external threaded portions of the respective associated drive shafts. Each of the above-discussed attachment portions 140-166 can be positioned adjacent the second ends 38, 46 of body members 14, 18, respectively, as shown in FIGS. 2, 6 and 7. The expansion mechanisms 26, 30 with their corresponding pairs of drive shafts 64, 68 and 72, 76 coupled about the sidewalls of body members 14, 18 can provide additional stability to the device 10, especially in an expanded state.

As will be discussed in greater detail below, driving gear members 80 of drive shafts 64 and 72 can drive meshing gear members 84 and thus corresponding drive shafts 68, 76 to expand and contract device 10. It should be appreciated that by driving gear members 80 in one direction, for example clockwise, to expand device 10, meshing gear members 84 will be driven in an opposite counterclockwise rotation. As a result, threaded portions 104 and 108 of expansion mechanism 26 can be of opposite hand (i.e., left and right hand thread patterns) and threaded portions 120 and 124 of expansion mechanism 30 can likewise be of opposite hand. In addition, as gear member 80 of expansion mechanism 26 turns in an opposite direction as gear member 80 of expansion mechanism 30, threaded portions 104 and 120 can be of opposite hand together with threaded portions 108 and 124 also being of opposite hand.

In a similar manner, lower threaded portions 112, 116 of expansion mechanism 26 can be of opposite hand relative to their respective upper portions 104, 108 so as to expand or drive the second body member 18 in an opposite direction as the first body member 14 is being expanded. In addition, lower threaded portions 128, 132 of expansion mechanism 30 can have an opposite thread hand configuration relative to each other and to their corresponding upper threaded portions 120, 124.

In one exemplary configuration, upper threaded portions 104, 108 of shafts 64, 68 can have respective right and left hand thread configurations, and upper threaded portions 120, 124 of shafts 72, 76 have respective left and right hand thread configurations. Based on this upper thread hand configuration, lower threaded portions 112, 116 of shafts 64, 68 can have respective left and right hand thread configurations, and lower threaded portions 128 and 132 of shafts 72, 76 can have right and left hand thread configurations. From this exemplary configuration, it can be seen that diagonally opposed shafts 64 and 76 can be identical, and diagonally opposed shafts 68 and 72 can likewise be identical, where shafts 64 and 76 have an overall opposite thread configuration as shafts 68 and 72, as shown for example in FIG. 2. It should be appreciated, however, that drive shafts 64, 68, 72 and 76 can have different thread configurations to expand and contract body members 14, 18 relative to each other.

The threaded portions of the drive shafts can each have the same axial length, which can determine the extent of axial expansion of the body members 14 and 18. In this regard, the length of the threaded portions can be sized to set or limit an amount of expansive movement of body members 14, 18. In one exemplary configuration, the threaded portions can have a longitudinal length substantially equal to a longitudinal length 174 of body members 14, 18, as shown for example in FIG. 6.

With the drive shafts 64, 68 and 72, 76 threadably coupled to body members 14, 18, the gear members 80, 84 can be positioned between the opposing first ends 34, 42 of the body members 14, 18, as shown in FIG. 1. In one exemplary configuration, the threaded portions of the drive shafts can be configured to maintain a spaced relationship between the first and second body members 14, 18 when body members 14, 18 are in the fully contracted position, as also shown in FIG. 1.

The amount of axial space between body members 14, 18 can be sized to accommodate attachment of the backstop 22 to drive shafts 64, 76, as will be discussed below.

The backstop 22 can include a body 180 having an arcuate shape complementary to an outer perimeter shape of the first and second body members 14, 18, as generally shown for example in FIGS. 1 and 5. In one exemplary configuration where the body members 14, 18 include a cylindrical shape, the backstop body 180 can include a complementary arcuate shape configured to be received in a recess 184 in each of body members 14, 18. In this configuration, the backstop 22 can extend circumferentially around the recessed perimeter of each body member by an amount less than 180 degrees, such as within a range of 150 to 170 degrees. It should be appreciated, however, that the backstop 22 can be sized to extend further or to a lesser amount around the body members 14, 18 than discussed above. The backstop 22 can include a longitudinal length that is sized so that when the device 10 is fully expanded, opposed ends 188 can be overlapping body members 14, 18, as shown in FIG. 3.

The backstop 22 can include a pair of attachment members 196 configured to engage the drive shafts 68 and 76, as shown for example in FIG. 5. In one exemplary configuration, the attachment members 196 can each include a pair of arms 200 having an arcuate shape that defines a corresponding pair of recesses 204. Each pair of arms 200 can be longitudinally spaced apart so as to receive one of the gear members 84 therebetween, as also shown in FIG. 5. The recesses 204 can be sized and shaped so as to create a snap-fit with non-threaded portions 208 of drive shafts 68 and 76 adjacent each side of the gear members 84. Additionally, the attachment members 196 can be positioned so as to be spaced apart by a slightly greater distance than the drive shafts 68, 76, so as to create a retention force urging the attachment members 196 toward the respective drive shafts in the installed configuration. A longitudinal height 212 of the attachment members 196 can additionally or in the alternative be used to determine the fully contracted or rest position of the body members 14, 18 relative to each other, as shown for example in FIGS. 1 and 6.

The backstop 22 can provide a barrier or backing in which to aid in packing bone growth material in the device 10 in a spinal implant procedure. Additionally, the backstop 22 can provide support for the body members 14, 18 while expanding and in the expanded state, particularly for sizes of the device having relatively long body members 14, 18 with correspondingly greater expansion lengths. The backstop 22 can remain stationary as the body members expand and contract relative to backstop 22.

With additional reference to FIGS. 8-8B, the modular endplates 12 will now be discussed in greater detail in connection with an attachment arrangement for coupling the endplates 12 to the expandable spinal implant device 10. The second ends 34, 42 of body members 14, 18 can include an attachment arrangement 220 configured to couple one of a variety of the modular endplates 12 thereto, which will be discussed below in greater detail. The attachment arrangement 220 can include a plurality of attachment members 224 extending longitudinally from an end surface 228 of the first and second body members 14, 18.

Figure 8:
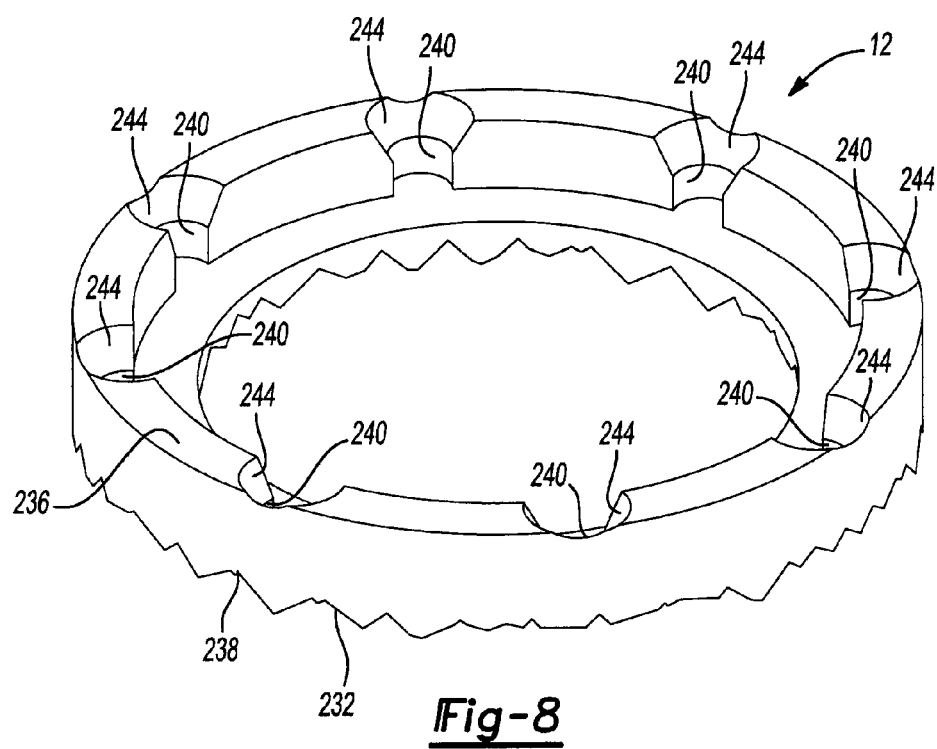
FIG. 8 is a perspective view of an exemplary modular endplate according to the principles of the present teachings.
Figures 8A, 8B:
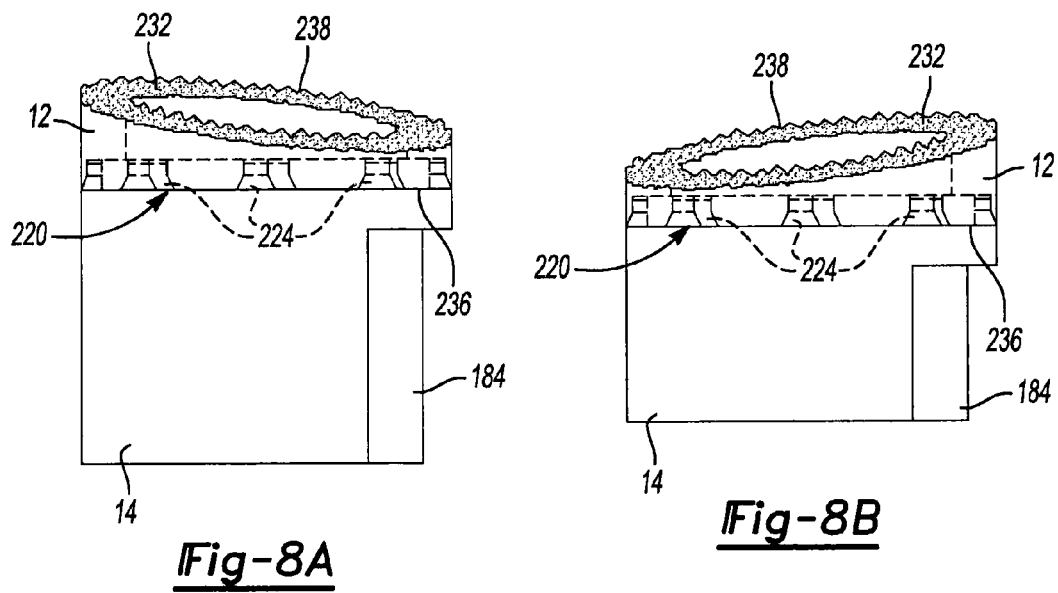
FIGS. 8A and 8B are exemplary views of modular endplates coupled to an exemplary expandable spinal implant device in different circumferential orientations according to the principles of the present teachings.

The modular endplates 12 can include a first or upper surface 232 configured to engage a vertebral body, and a second or lower surface 236 configured to engage one of the end surfaces 228 of the body members 14, 18, as shown in FIGS. 8-8B. The modular endplates 12 can be formed of a suitable biocompatible metallic material, such as titanium or titanium alloy, that is either solid or porous. The first surface 232 can include a plurality of peaks, ridges, teeth, or the like 238 configured to enhance engagement with the vertebral body. The second surface 236 can include a plurality of closed end apertures 240 corresponding to the number of attachment members 224. Each aperture 240 can include a chamfer 244 to aid in receiving the attachment members 224 therein. The apertures 240 can be sized relative to attachment members 224 to create an interference or press-fit relationship. In this regard, when the modular endplates 12 are positioned on the end surfaces 228, the attachment members 224 will be received in the apertures 240 in a press-fit manner to removably secure the endplates 12 to the respective body members 14, 18. It should be appreciated that the attachment members 224 can alternatively extend from the second surface 236 of modular endplate 12 and the apertures 240 can alternatively be formed into end surface 228 of body members 14 and/or 18.

The first surface 232 of the modular endplates 12 can be orientated parallel to the second surface 236, or can be provided in a variety of angles relative to the second surface 236, as shown for example in FIGS. 2, 3 and 8A-8B. By providing the modular endplates 12 with a variety of angled first surface configurations, the expandable spinal implant device 10 can accommodate various vertebral body and spinal orientations, as may be presented during spinal implant procedures of different patients. In addition, the attachment configuration for the modular endplates 12 can provide an ability to circumferentially orient the modular endplates 12 relative to the body members 14, 18 in a variety of positions, as shown for example in FIGS. 8A and 8B.

Figure 26:
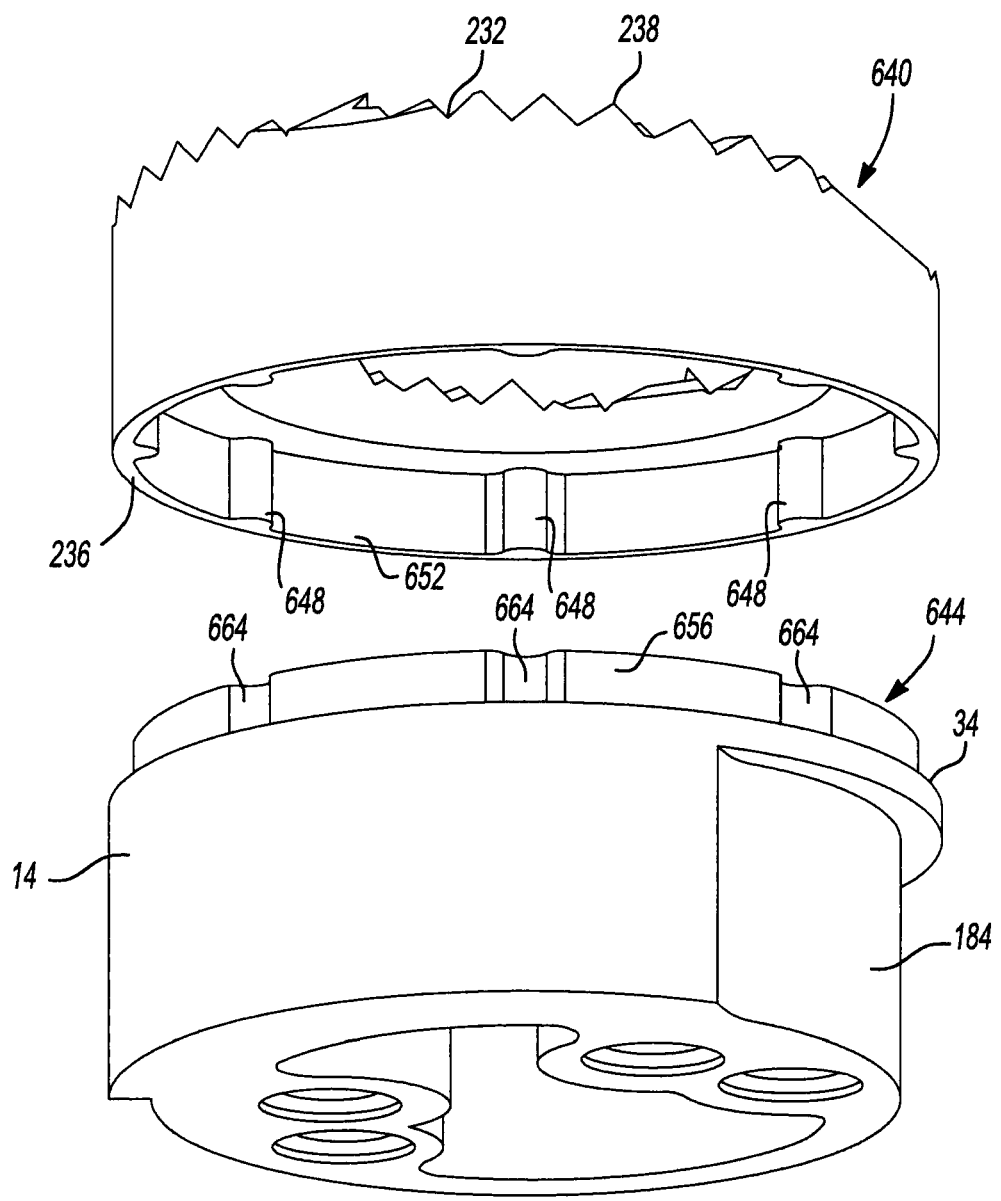
FIG. 26 is a perspective view of an exemplary alternative modular endplate and associated attachment arrangement according to the principles of the present teachings.

As can be appreciated, the number of attachment members 224 can dictate the number of different circumferential positions that the modular endplates 12 can be coupled to the body members 14, 18. For example, if a surgeon determines that an angled modular endplate 12 is desirable in a spinal implant procedure, the surgeon can further determine an optimal circumferential orientation of the angled surface and couple the angled modular endplate 12 to the respective body member 14 in the desired orientation. Further, the removable nature of the press-fit coupling arrangement allows the modular endplates 12 to be removed for adjustment, if necessary. In addition, the first and second body members 14, 18 can carry the same or different modular endplates 12, as shown for example in FIGS. 1 and 2. An alternative modular endplate 640 and associated attachment arrangement 644 is shown in FIG. 26 and will be discussed in greater detail below.

Figures 9, 10:
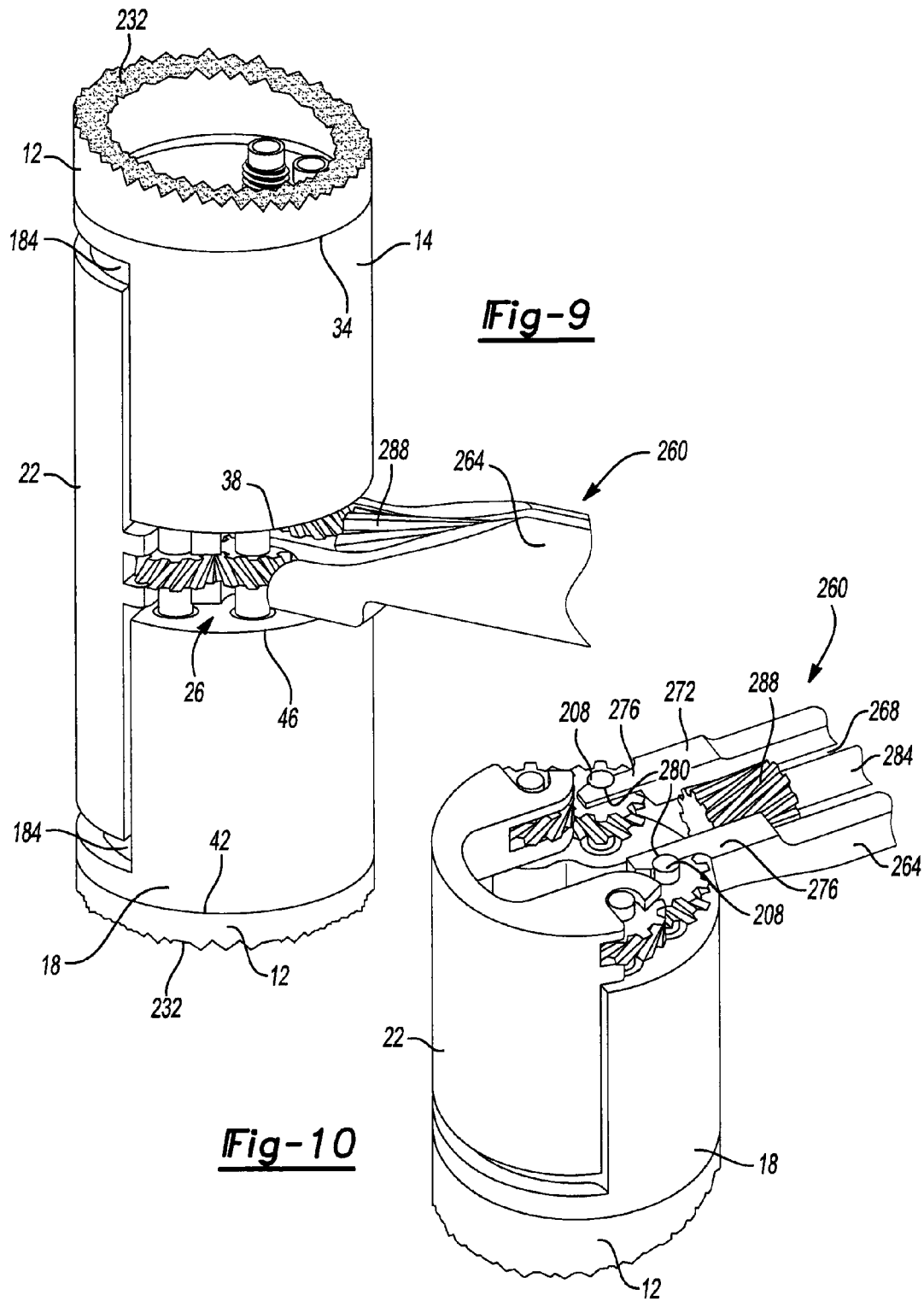
FIGS. 9 and 10 are partial perspective views of an exemplary instrument associated with an expandable spinal implant device according to the principles of the present teachings.

With additional reference to FIGS. 9-10, an instrument 260 for use in expanding and contracting the expandable spinal implant device 10 will now be discussed. The instrument 260 can include a housing 264 having an internal passage 268 and a first end 272 configured to be removably coupled to the device 10. A pair of attachment arms 276 can extend longitudinally from the first end 272 and can each include a recess 280 formed on an inner side thereof for engaging one of the non-threaded portions 208 of drive shafts 64, 72, as shown for example in FIG. 10. In one exemplary configuration, the attachment arms 276 can be spaced apart a greater distance than the drive shafts 64, 72 so as to provide a biasing force to urge the recesses 280 against the respective drive shafts when coupled thereto.

The instrument 260 can further include drive member 284 rotatably and axially moveable within passage 268 of housing 264. The drive member can include a drive gear 288 having a gear tooth pattern configured for selective intermeshing engagement with the gear members 80 of drive shafts 64, 72. With the housing coupled to drive shafts 64, 72 as discussed above, the drive member 284 can be axially advanced relative to the housing 264 to place drive gear 288 into simultaneous driving engagement with each gear member 80.

With continued reference to FIGS. 1-10, operation and use of the expandable spinal implant device 10 will now be discussed in further detail. Initially, a surgeon can select an expandable spinal implant device 10 having a suitable length 174, as well as select one of the modular endplate configurations 12 for the body members 14, 18 based on the needs of a specific patient. If angled modular endplates 12 are selected, the endplates can be circumferentially orientated or "dialed in" to an optimal orientation for engagement with the superior or inferior vertebral bodies. In an exemplary corpectomy procedure, the expandable spinal implant device 10 can initially be positioned in the space between the superior and inferior vertebral bodies where one or more vertebrae or discs have been removed.

The instrument 260 can be removably coupled to the drive shafts 64, 72 and the drive member 284 can be advanced to place drive gear 288 in meshing engagement with gears 80. Drive member 284 can then be rotated to simultaneously drive gear members 80 of drive shafts 64, 72, which in turn will drive gear members 84 of drive shafts 68 and 76. It should be appreciated that the instrument 260 can simultaneously drive the four drive shafts 64, 68, 72 and 76 by simultaneously driving gear members 80 as discussed above. In driving gear members 80 in one direction, say clockwise, each of the drive shafts can rotate as discussed above to expand the body members 14, 18 along the longitudinal axis 60 so that the body members move away from each other to increase an overall length of the spinal implant device 10. This can be seen, for example, by a comparison of the spinal implant device in FIG. 2 in the expanded state versus the device 10 in FIG. 1 in the unexpanded or contracted state. As the body members are expanded or contracted with the instrument 260, the body members can axially translate in sliding engagement relative to backstop 22.

The instrument 260 can be used to expand body members 14, 18 until the modular endplate 12 engage the respective superior and inferior vertebral bodies. Instrument 260 can then be removed from drive shafts 64, 72. The expanded device 10 can maintain the expanded position by virtue of the multiple drive shafts with different thread orientations engaging each body member 14, 18. In this regard, it should be appreciated that the drive shafts 64, 68 and 72, 76 do not passively back drive such that they maintain the expanded position discussed above. To contract device 10, the drive member 284 can be rotated in an opposite direction as used to expand the device, say counterclockwise, to actively back drive the drive shafts and draw the body members 14, 18 toward each other.

During expansion and contraction of the device 10, the drive shafts can rotate relative to the body members 14, 18 and thereby transform the rotational movement into axial translation of body members 14, 18 via the threaded connection between the internal threads 152 of the attachment portions 140-166 and the threaded portions of the drive shafts. It should be appreciated that the gear members 80 can alternatively be driven in a counterclockwise direction to expand device 10 and in a clockwise direction to contract the device.

Figure 11:
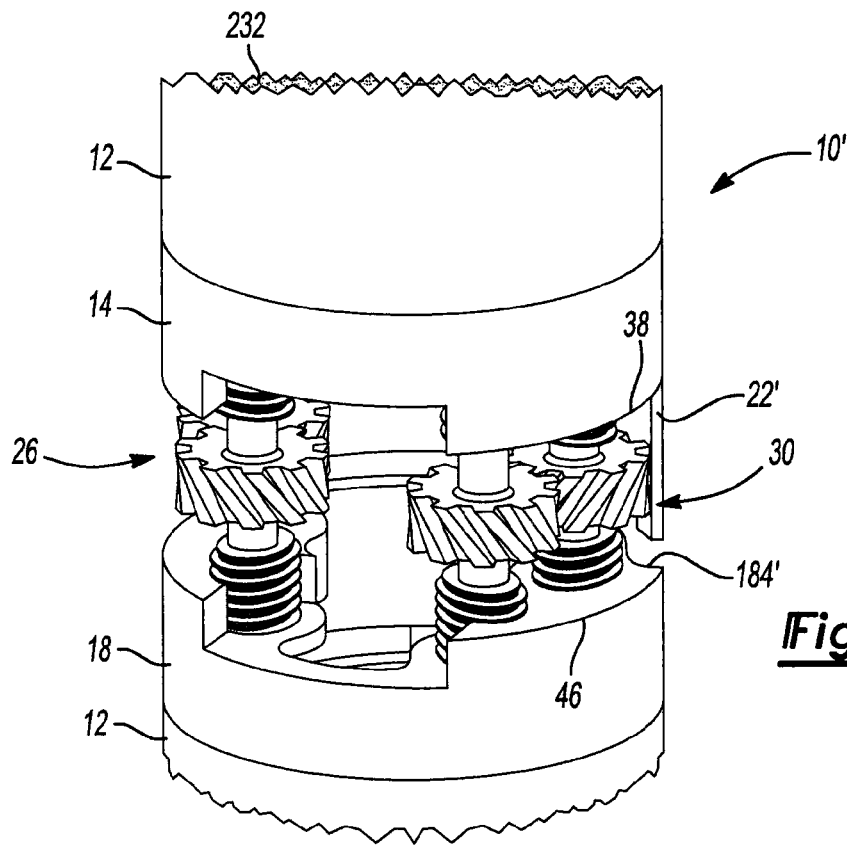
FIG. 11 is a perspective view of an exemplary expandable spinal implant device carrying modular endplates according to the principles of the present teachings.
Figure 12:
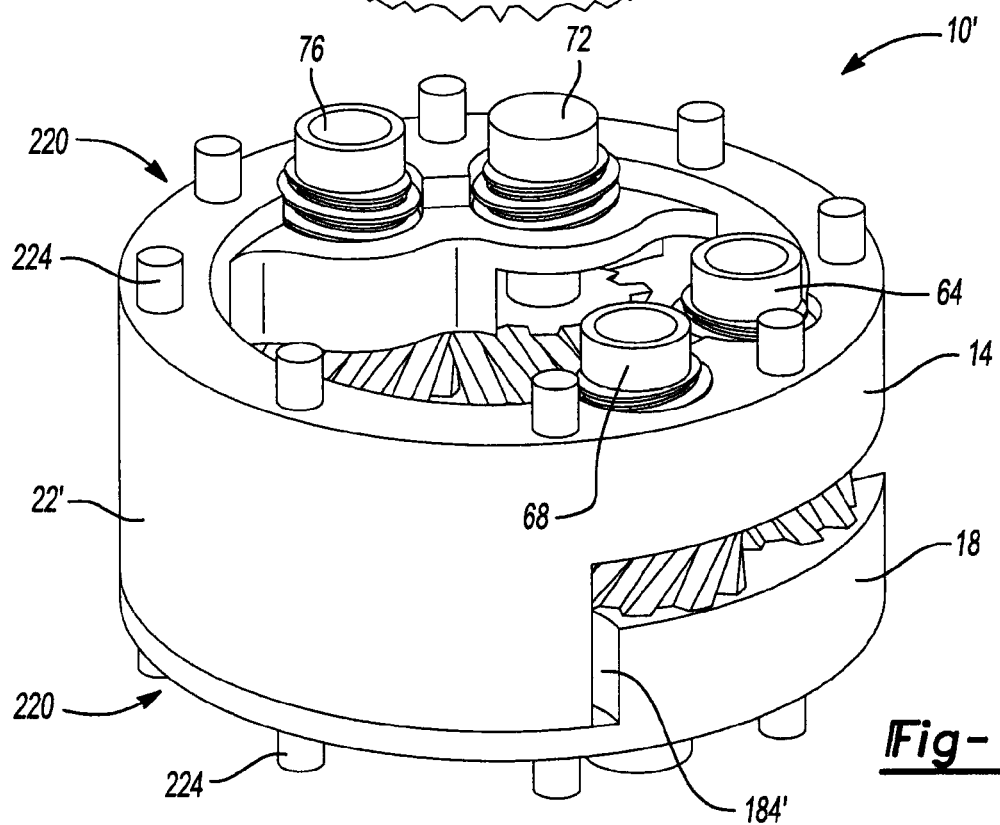
FIG. 12 is a perspective view of the expandable spinal implant device of FIG. 11 with the modular endplates removed.
Figure 13:
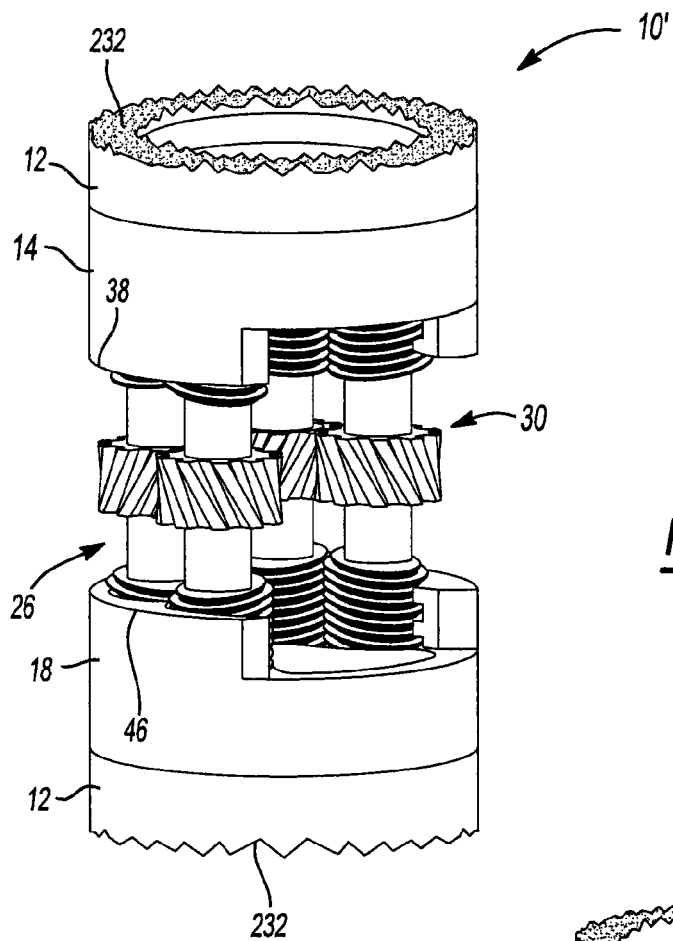
FIG. 13 is a perspective view of the expandable spinal implant device of FIG. 11 in an expanded state and carrying an alternative exemplary modular endplate according to the principles of the present teachings.

Turning now to FIGS. 11-13, an expandable spinal implant device 10' will now be discussed according to an aspect of the present teachings. Device 10' is similar to device 10 such that only differences between the expandable spinal implant devices 10 and 10' will now be discussed. Like reference characters have been used to identify elements similar to those previously introduced.

Expandable device 10' can include an integral backstop member 22' as opposed to the separate backstop 22 coupled to the drive shafts 68, 76. Backstop 22' can be integrally formed with one of the body members 14, 18 and longitudinally extend from the second end 38 or 46. In one exemplary configuration, backstop 22' can extend from the second end 38 of first body member 14, as shown in FIGS. 11 and 12. The second body member 18 can include a corresponding recessed area or cutout 184' to accommodate backstop 22', as also shown in FIGS. 11 and 12. In one exemplary configuration, the integrally formed backstop 22' can be used with expandable spinal implant devices 10' that include a longitudinal length 174 less than those of the devices 10 with a separately incorporated backstop 22.

The expandable spinal implant device 10' can also include body members 14, 18 of varying diameters, some of which can be smaller than provided with the expandable spinal implant devices 10. In such smaller diameter devices 10', the drive shafts 68 and 76 can be positioned radially inward of the drive shafts 64, 72, as shown for example in FIG. 13. As the drive shafts are positioned about the sidewall, this configuration can accommodate smaller diameter body members, as opposed to the larger diameter body members where the drive shafts 68, 76 are radially outboard of the drive shafts 64, 72, as shown for example in FIGS. 2 and 11. In each of the expandable spinal implant devices 10, 10', the drive shafts 64, 72 can be spaced apart by the same distance such that only one instrument 260 can be required to operate the devices 10, 10'. Operation of the expandable spinal implant device 10' can be substantially similar or the same as device 10 and thus reference is made to the above discussion of the operation of device 10.

While the expandable spinal implant devices 10 and 10' have been discussed above as carrying removably coupled modular endplates 12, it should be appreciated that one or both of the body members 14, 18 can alternatively include integrally formed endplates having teeth or the like 238 on a bone engaging surface thereof.

Figure 14:
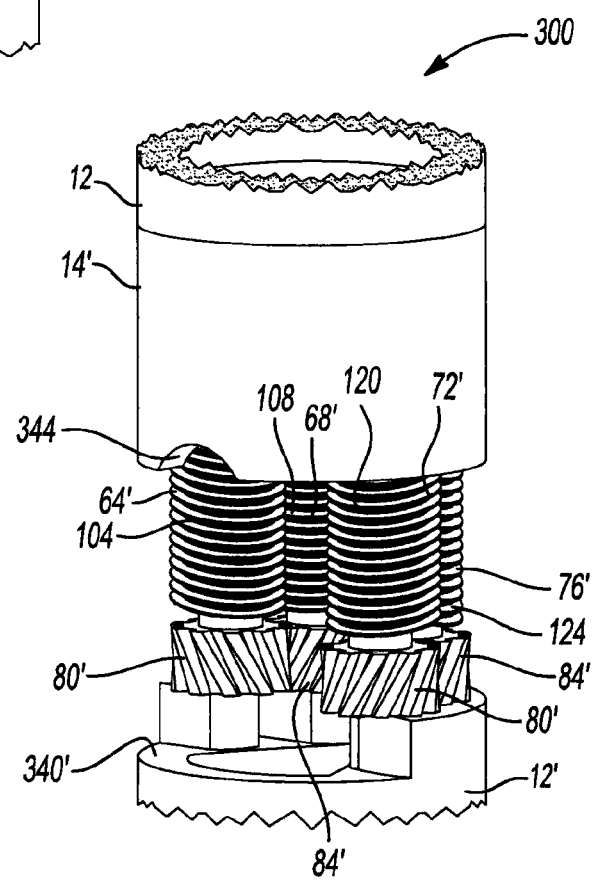
FIG. 14 is a perspective view of an exemplary expandable spinal implant device carrying a modular endplate according to the principles of the present teachings.
Figure 15:
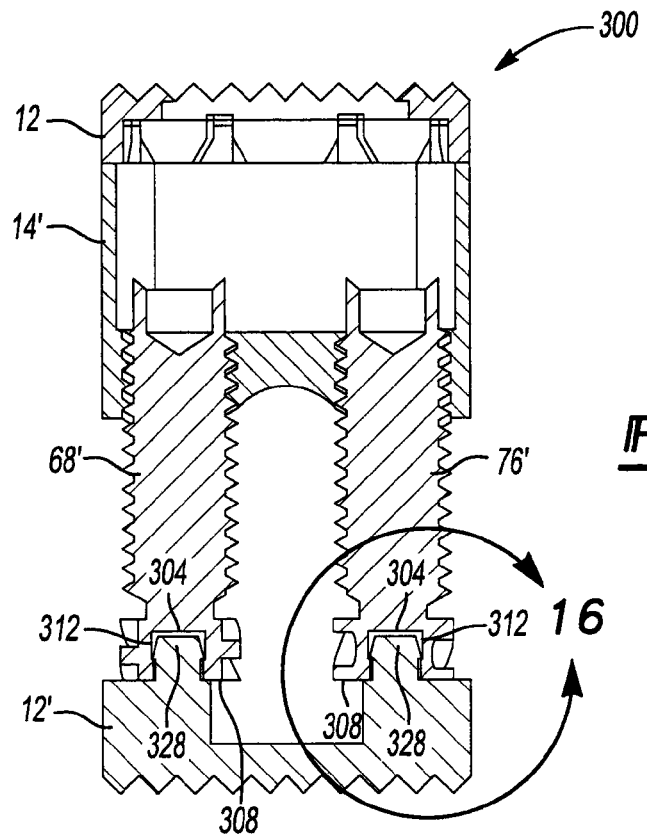
FIG. 15 is a cross-sectional view of the expandable spinal implant device of FIG. 14.
Figure 16:
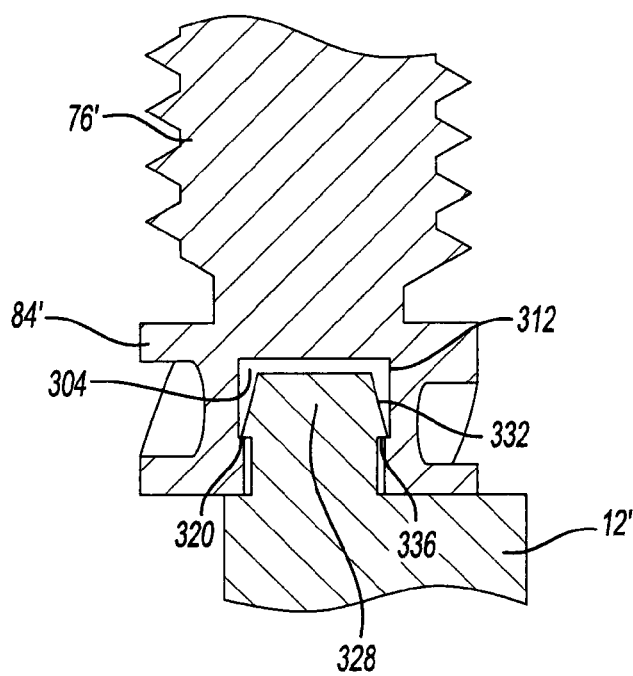
FIG. 16 is an enlarged view of a coupling arrangement illustrated in FIG. 15.

Turning now to FIGS. 14-16, an expandable spinal implant device 300 is shown according to an aspect of the present teachings. As with device 10', device 300 can include several features of device 10 such that only differences between the expandable spinal implant devices 10 and 300 will now be discussed. Like reference characters have been used to identify elements similar to those previously introduced. In general, device 300 can be essentially the same as an upper portion of device 10 from the gear members 80, 84 to the first end of body member 14, as generally shown in FIG. 14.

Device 300 can include drive shafts 64' 68', 72' and 76' having gear members 80', 84' and corresponding threaded portions 104, 108, 120 and 124 coupled to body member 14', as discussed above with reference to device 10. In place of the second body member 18, gear members 80', 84' can be directly coupled to an attachment feature of a modified endplate 12'. In this manner, gear members 80', 84' can include an aperture 304 on a side 308 opposite the side facing the respective threaded portions, as shown in FIGS. 15 and 16. Aperture 304 can include a larger diameter area 312 spaced inward from side 308 and forming a shoulder 320.

Modular endplate 12' can include an attachment feature 328 extending axially therefrom and configured to be received in the corresponding apertures 304. Attachment feature 328 can include a projecting member 332 having a barb 336 on an end thereof. The barb can include a width or diameter sufficient to engage the shoulder 320 to rotatably couple the modular endplate 12' to the gear members 80', 84'. The gear members 80, 84' can rotate relative to the modular endplate 12' when driven by drive gear 288 of instrument 260. Modular endplate 12' can further include a recessed area 340 and body member 14' can likewise include a recessed area 344 to accommodate instrument 260.

In operation, drive gear 288 can drive gear members 80', which in turn can drive gear members 84 to expand or contract body member 14' relative to modular endplate 12' in a manner similar to that discussed above. It should be appreciated that while expandable spinal implant device 300 has been discussed with first body member 14' expanding and contracting, device 300 could alternatively be configured to have second body member 18' be drivable relative to modular endplate 12'.

Figure 17:
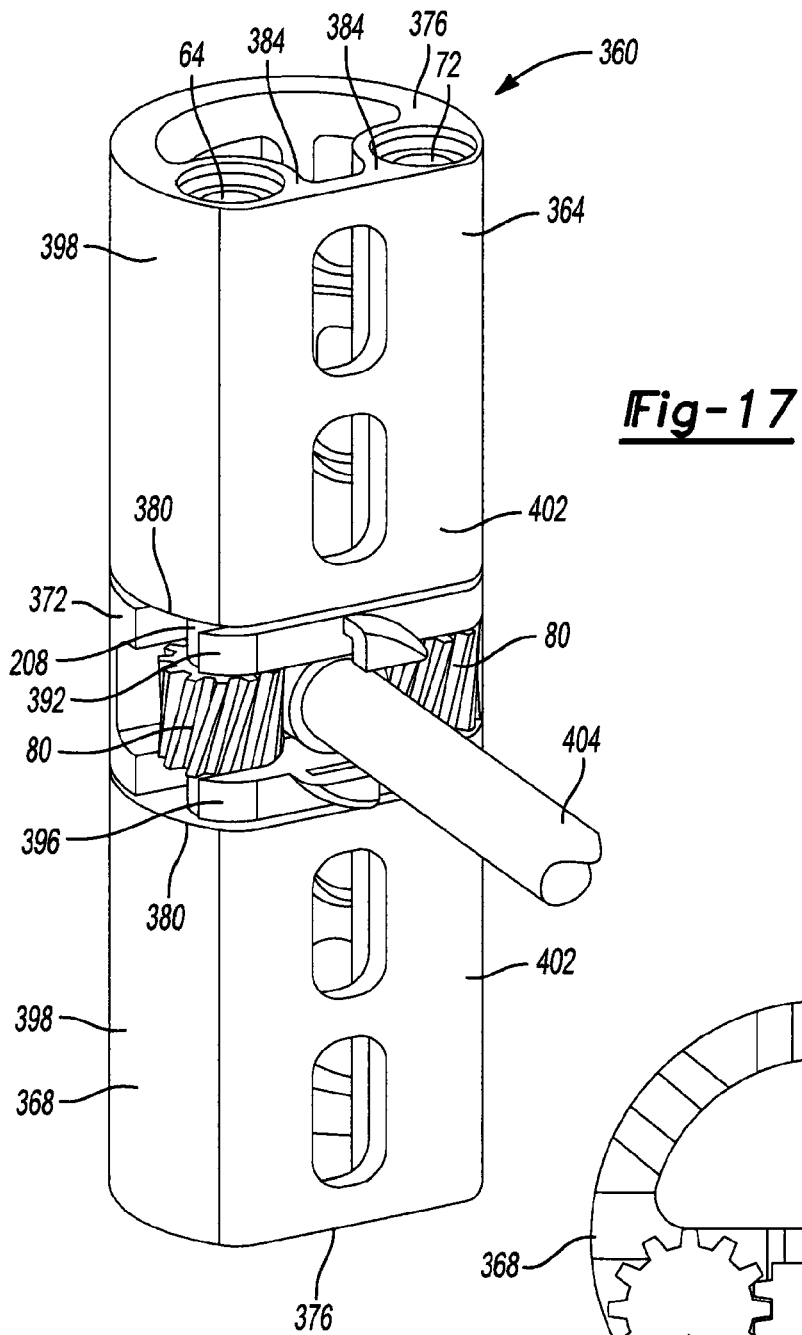
FIG. 17 is a perspective view of an exemplary expandable spinal implant device with an associated instrument according to the principles of the present teachings.
Figure 18:
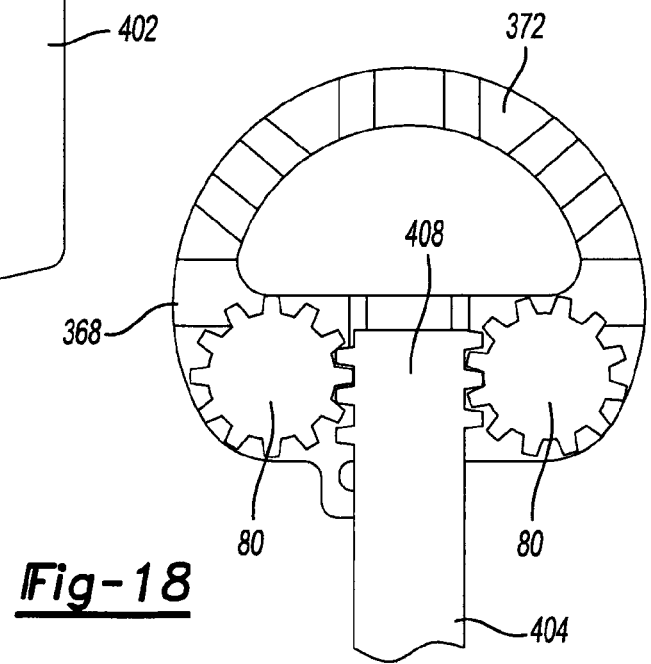
FIG. 18 is a partial top view of the expandable spinal implant device and instrument of FIG. 17.

Turning now to FIGS. 17 and 18, an expandable spinal implant device 360 is shown according to an aspect of the present teachings, where like reference characters have been used to identify elements similar to those previously introduced. Device 360 can include a first body member 364, a second body member 368 and a central body member 372 positioned therebetween. First and second body members 364, 368 can each include a first end 376 and a second opposite end 380 facing the central body member 372.

A pair of drive shafts 64, 72 can be threadably coupled to internally threaded attachment portions 384 positioned about a sidewall 388 of body members 364, 368 in a manner similar to that discussed above with respect to device 10. The central body member 372 can be coupled to the drive shafts 64, 72 via first and second attachment arms 392 and 396. In an alternative configuration, central body member can be coupled to drive shafts 64, 72 using only the second attachment arms 396 so as to provide an area for coupling instrument 260, as will be discussed below. In one exemplary configuration, body members 364 and 368 can include a substantially cylindrical shape 398 with a flattened portion 402 along a front surface thereof, as shown for example in FIG. 17.

An instrument 404 having a drive gear 408 at an end thereof can be used to drive gear members 80 to expand and contract body members 364, 368 in a manner similar to that discussed with reference to device 10. Alternatively, instrument 260 can be used to drive gear members 80, where cut-outs can be provided in the central body member so that arms 200 can engage non-threaded portions 208 of drive shafts 64, 72.

Figure 19:
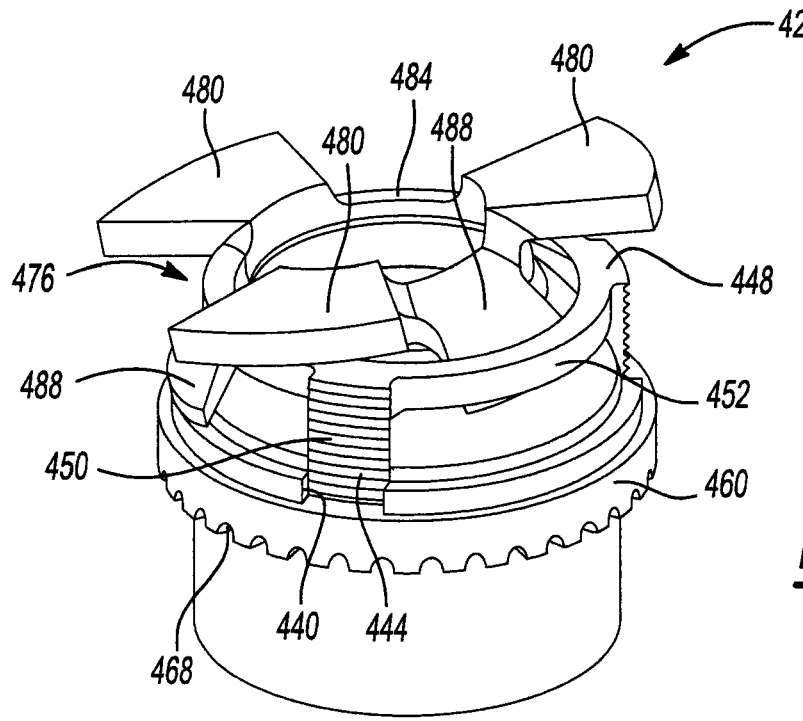
FIG. 19 is a perspective view of an exemplary articulating endplate according to the principles of the present teachings.
Figure 20:
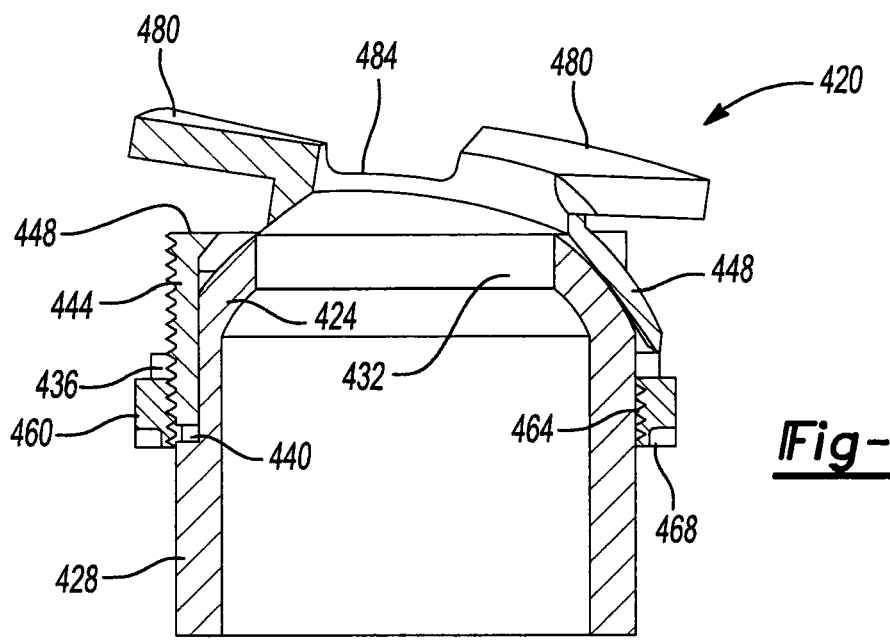
FIG. 20 is a cross-sectional view of the articulating endplate of FIG. 19.

Turning now to FIGS. 19 and 20, an alternative articulatable endplate assembly 420 is shown according to an aspect of the present teachings. Endplate assembly 420 can be used with each of the above-discussed expandable spinal implant devices, where the attachment arrangement 220 and first ends of applicable body members would be modified as discussed below. For discussion purposes, FIGS. 19 and 20 will be discussed with reference to first body member 14, while noting that the discussion is equally applicable to each of the above-discussed body members.

To accommodate endplate assembly 420, the first end 34 of body member 14 can alternatively include a convex and/or spherical portion 424 extending from sidewall 428 and defining a central opening 432, as shown for example in FIG. 20. A substantially annular collar 436 can extend radially outward from sidewall 428 proximate a transition between sidewall 428 and convex portion 424. Collar 436 and convex portion 424 can each include recessed areas 440 for receiving threaded posts 444 of a lock ring 448, as will be discussed below in greater detail.

The lock ring 448 can include an annular member 452 having a diameter smaller than a diameter of the convex portion 424 adjacent collar 436. The threaded posts 444 can include external threads 450 and can extend axially in a direction toward collar 436 so as to be positioned in recessed areas 440, as shown in FIG. 19. A threaded ring 460 can be positioned on an opposite side of the collar 436 as convex portion 424. The threaded ring 460 can include a threaded inner surface 464 facing sidewall 428 and a lower surface having a gear tooth arrangement 468 thereon. The threaded surface 464 can threadably engage the external threads of posts 444, as shown in FIG. 20.

An articulatable endplate 476 can be positioned between the lock ring 448 and the convex portion 424, as shown in FIGS. 19 and 20. Endplate 476 can include a plurality of bone engaging members 480 extending from a central region 484 and a plurality of device engaging members 488 extending from the central region 484 and positioned between a pair of the bone engaging members 480. The device engaging members 488 can extend at an acute angle relative to the bone engaging members 480 and can have a shape substantially conforming with a shape of convex portion 424, as shown for example in FIG. 20. The device engaging members 488 can extend between the convex portion 424 and the lock ring 448.

In operation, endplate 476 can articulate relative to convex portion 424 until locked into a selected position via lock ring 448 and threaded ring 460. Once a desired position for endplate 476 is determined, threaded ring 460 can be rotated to draw posts 444 downward and thus annular member 452 against device engaging members 488. Device engaging members 488 can thus be compressed between annular member 452 and convex portion 424 thereby creating a friction lock and locking articulatable endplate 476 in the desired position. To adjust the position of endplate 476, threaded ring 460 can be rotated in an opposite direction as that for tightening the lock ring 448, thereby raising the annular member 452 relative to convex portion 424 and thus releasing device engaging members 488. An instrument (not shown) can be used to rotate threaded ring 460 relative to posts 444 and annular collar 436 by engaging the gear tooth arrangement 468.

Figure 25:
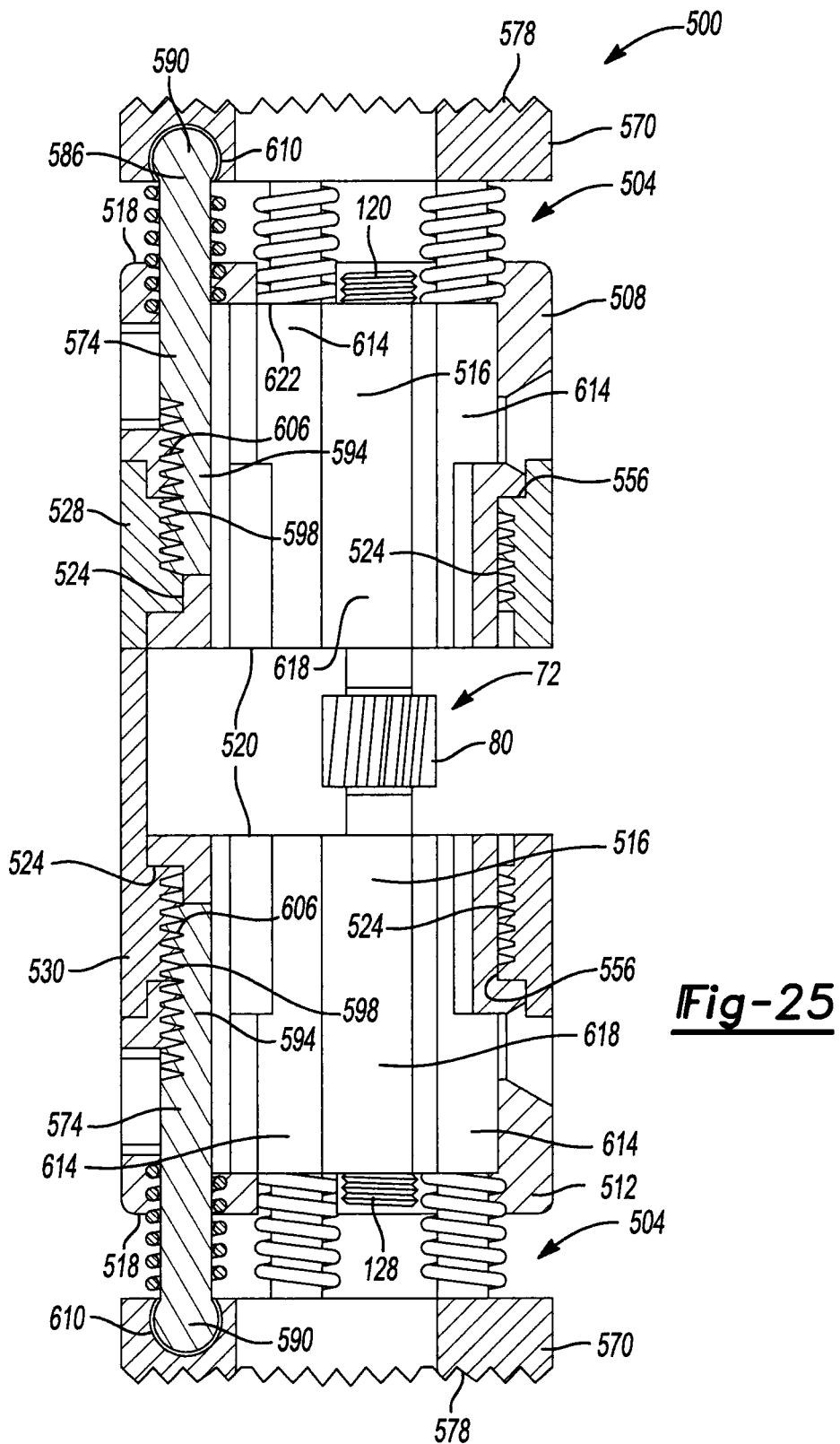
FIG. 25 is a cross-sectional view of the expandable spinal implant device of FIG. 21 according to the principles of the present teachings.

Turning now to FIGS. 21-25, an expandable spinal implant device 500 having articulating endplate assemblies 504 is shown according to an aspect of the present teachings, where like reference characters have also been used to identify elements similar to those previously introduced. Device 500 can include a first or superior body member 508, a second or inferior body member 512 and drive shafts 64 and 72. First and second body members 508, 512 can include internally threaded attachment portions 516 for threadably receiving respective upper threaded portions 104, 120 and lower threaded portions 112, 128 of drive shafts 64, 72, as generally shown in FIGS. 21 and 25 with reference to drive shaft 72.

First and second body members 508, 512 can each include a first end 518 and an opposite second end 520. An annular recessed area 524 can be provided in each body member 508, 512 proximate the second ends 520, as generally shown in FIG. 25. Device 500 can further include first and second intermediate body members 528, 532 each having an annular portion 536 defining a first end 540, a second end 542, and a projecting portion 544 extending axially from a portion of the second end 542. A sidewall 552 of each intermediate member 528, 532 can include circumferentially spaced apart raised engagement portions 556 extending radially inwardly from the sidewall 552, as generally shown in FIG. 25 with reference to FIG. 24. Raised engagement portions 556 can include serrated teeth 560 on an inner surface thereof. The intermediate body members 528, 532 can be rotatably coupled to the respective first and second body members 508, 512 such that the raised engagement portions 556 are received in the respective annular recessed areas 524, as shown in FIG. 25.

The endplate assemblies 504 can each include an annular ring 570 and a plurality of posts 574 pivotally coupled thereto.

The annular ring 570 can include a first bone engaging surface 578 and a second device facing surface 582. The plurality of posts 574 can include a first end 586 having a spherical attachment area 590 and a second end 594 having a radially outward facing engagement area 598 with a plurality of serrated teeth 606 disposed thereon. The second surface 582 of annular ring 570 can include a plurality of recessed attachment portions 610 having a spherical shape complementary to the spherically shaped attachment area of posts 574. The first end 568 of posts 574 can be pivotally coupled to the annular ring 570 via the recessed attachment portions 610, as shown in FIG. 25. In one exemplary configuration, the posts 574 can be coupled to the annular ring 570 via a snap-fit pivotal coupling arrangement.

Endplate assemblies 504 can be slidably coupled to the respective first and second body members 528, 532 via posts 574. In particular, the second end 594 of each post 574 can be slidably received in an attachment bore 614 formed about a sidewall 618 of body members 508, 512, as shown for example in FIG. 25. The recessed area 524 can extend into the attachment bore 614 such that when the posts 574 are positioned in the bore 614, the engagement area 598 is exposed to the recessed area 524 and annular portion 536 of the respective intermediate members 528, 532. Each post 574 can include a spring 620 extending between the annular ring 570 and a top surface 622 of bores 614. In one exemplary configuration, spring 620 can bias annular rings 570 away from the respective body members 508, 512.

With particular reference to FIGS. 24 and 25, the intermediate members 528, 532 can include a gear tooth pattern 626 disposed about the first ends 540 thereof and configured to mesh with a pinion gear 630 of an instrument 634. Instrument 634 can be used to separately rotate each of the intermediate members 512, 532 relative to their respective body members 508, 512 to engage or disengage the teeth 560 of the raised engagement portions with the teeth 606 of posts 574. In this manner, each post 574 can be individually positioned relative to body members 508 and/or 512 to obtain a desired orientation of endplate annular ring 570 and the intermediate member 528, 532 can then be rotated to lock each post 574 in the desired position.

When the expandable spinal implant device 500 is in a contracted state, as shown in FIGS. 21-25, the projecting portion 544 of intermediate member 528 can engage the second end 542 of intermediate member 532. Similarly, the projecting portion 544 of intermediate member 532 can engage the second end 542 of body intermediate member 528, as shown for example in FIGS. 21 and 22. In one exemplary configuration, the first and second body members 508, 512 and first and second intermediate members 528, 532 can be coaxially disposed and can include the same outer diameters.

In operation, expandable spinal implant device 500 can be expanded and contracted via drive shafts 64, 72 in the same or substantially the same manner as discussed with respect to expandable spinal implant device 360. Independent of the expanding or contracting of device 500, each articulatable endplate assembly 504 can be individually adjusted relative to a respective body member 508, 512 to obtain a desired orientation of the bone engaging surface 578. For example, in an expanded state of device 500, intermediate member 528 can be rotated to disengage teeth 560 from teeth 606 of posts 574. The annular ring 570 can then be adjusted to one of a plurality of different orientations where the posts 574 can be axially adjusted relative to body member 508 and the annular ring 570 can pivot about the spherical attachment areas 598.

Once a desired orientation of the annular ring 570 is achieved, the intermediate member 528 can be rotated to engage the teeth 560 with the teeth 606 and thereby lock each post in position and thus the annular ring in the desired position. It should be appreciated that the endplate assembly 504 associated with body member 512 can operate in the same manner. Further, it should be appreciated that while endplate assemblies 504 have been discussed in connection with expandable spinal implant device 500, the endplate assemblies 504 can also be incorporated into one or more of the other expandable spinal implant devices discussed above.

Turning now to FIG. 26, the alternative modular endplate 640 and associated attachment arrangement 644 will now be discussed, where like reference numerals refer to like features previously introduced in connection with the discussion of modular endplate 12. Modular endplate 640 is similar to modular endplate 12, such that only differences between the endplates will now be discussed. In this regard, it should be appreciated that modular endplate 640 includes the first surface 232 that can be parallel to the second surface 236 or angled relative thereto, as discussed above with modular endplate 12. Modular endplate 640 can also be removably positioned in a variety of circumferential orientations relative to body members 14 and/or 18 in a similar manner as modular endplate 12.

Modular endplate 640 can include a plurality of axially extending projections 648 protruding radially inwardly from an inner sidewall 652 of endplate 640, as shown in FIG. 26. Attachment arrangement 644 can include a circumferentially recessed portion 656 at the first end 34 and/or 42 of body members 14 and/or 18. Recessed portion 656 can include a plurality of depressions 664 corresponding to the number of projections 648 of modular endplate 640. Depressions 664 can be sized and shaped to receive the projections 648 in a press-fit relationship to removably secure modular endplate 640 to body members 14 and/or 18 in a variety of circumferential orientations.

While specific examples have been discussed in the specification and illustrated in the drawings, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless discussed otherwise above. Moreover, many modifications may be made to adapt a particular situation or material to the present teachings without departing from the essential scope thereof. Therefore, it may be intended that the present teachings not be limited to the particular examples illustrated by the drawings and discussed in the specification as the best mode of presently contemplated for carrying out the present teachings but that the scope of the present disclosure will include any embodiments following within the foregoing description and any appended claims.

What is claimed is:

1. An expandable spinal implant device for supporting vertebral bodies comprising:
    a first body member and a second body member each having first and second ends and defining a hollow interior, the first ends positionable toward a respective one of the vertebral bodies, a convex portion formed about the first end of each body member;
    a first pair of drive shafts and a second pair of drive shafts spaced apart from the first pair of drive shafts, the respective drive shafts of each pair of drive shafts having a gear member rotationally coupling the respective drive shafts to each other, each pair of drive shafts threadably engaged at a first side to the first body member and at a second side to the second body member; and a pair of articulating endplates moveably coupled to the respective first ends, the articulating endplates configured to pivot about the respective convex portions;

wherein the first and second pairs of drive shafts are operable to effect axial displacement of the first body member relative to the second body member by rotationally driving one of the gear members of each pair of drive shafts, and wherein each articulating endplate includes a bone engagement portion, a device engaging portion and a lock ring, the device engaging portion configured to pivot about one of the convex portions, the lock ring configured to selectively compress the device engaging portion against a surface of the convex portion in a desired position to secure the respective endplate to the respective body member in the desired position.

2. The expandable spinal implant of claim 1, further comprising an annular collar radially extending from a sidewall of each body member proximate the convex portion and a ring member rotationally coupled to the respective first and second body members adjacent the annular collar, each ring member being threadably coupled to a respective lock ring.

3. The expandable spinal implant of claim 2, wherein rotating the ring members draws the respective lock ring against the respective device engaging portion thereby compressing the device engaging portion against the respective convex portion to lock the respective articulating endplate in the desired position.

4. The expandable spinal implant of claim 2, wherein each lock ring includes an annular member having an internal diameter smaller than a diameter of the convex portion, and a plurality of threaded posts extending axially therefrom, the threaded posts threadably engaging the ring member.

5. The expandable spinal implant device of claim 1, wherein the first and second body members are rotationally fixed by the first and second pairs of drive shafts, and wherein the respective drive shafts of each pair of drive shafts are directly coupled to each other by the respective gear member.

6. The expandable spinal implant device of claim 1, wherein the second ends of the first and second body members are spaced apart from and opposing each other in an unexpanded and an expanded position of the body members and during movement therebetween, and wherein each of the gear members are positioned between and axially spaced apart from the second ends of the body members in both the unexpanded and the expanded positions.

7. The expandable spinal implant device of claim 1, wherein the first and second pairs of drive shafts and associated gear members are cooperatively configured such that driving the one of the gear members of each pair of drive shafts simultaneously drives each pair of drive shafts to effect axial displacement of the first and second body members, and wherein the gear members of the respective drive shafts of each pair of drive shafts are directly rotationally coupled to each other.

8. The expandable spinal implant device of claim 1, wherein the first side of each drive shaft of each pair of drive shafts has an opposite thread angle as the second side of each drive shaft of each pair of drive shafts.

9. The expandable spinal implant device of claim 8, wherein the first pair of drive shafts includes first and second drive shafts, the first and second drive shafts having opposite thread angles at each of the first and second sides, and wherein the second pair of drive shafts includes third and fourth drive shafts, the third and fourth drive shafts having opposite thread angles at each of the first and second sides.

10. The expandable spinal implant device of claim 1, further comprising a central body portion extending from the second end of one of the first and second body members, the central body portion being received in a recess formed in the other one of the first and second body members.

11. An expandable spinal implant device for supporting vertebral bodies comprising:

a first body member and a second body member each having first and second ends and defining a hollow interior, the first ends of each body member positionable toward a respective one of the vertebral bodies, a convex portion formed about the first end of each body member;

first and second articulating endplates moveably coupled to a respective first end, each articulating endplate configured to pivot about one of the convex portions, each articulating endplate includes a bone engagement portion, a device engaging portion and a lock ring, the device engaging portion configured to pivot about one of the convex portions, the lock ring configured to selectively compress the device engaging portion against a surface of the convex portion in a desired position to secure the respective endplate to the respective body member in the desired position; and an annular collar radially extending from a sidewall of each body member proximate the convex portion and a ring member rotationally coupled to the respective first and second body members adjacent the annular collar, each ring member being threadably coupled to a respective lock ring, wherein rotating the ring members draws the respective lock ring against the respective device engaging portion thereby compressing the device engaging portion against the respective convex portion to lock the respective articulating endplate in the desired position.

12. The expandable spinal implant device of claim 11, further comprising:

a first pair of drive shafts and a second pair of drive shafts spaced apart from the first pair of drive shafts, the respective drive shafts of each pair of drive shafts having a central gear member rotationally coupling the respective shafts to each other, each pair of drive shafts threadably engaged at a first side to the first body member and at a second side to the second body member;

a central body member coupled to at least one shaft of the first and second pairs of drive shafts and configured to slidably engage an exterior surface of the first and second body members; and wherein the first and second pairs of drive shafts are operable to effect axial displacement of the first body member relative to the second body member by rotationally driving one of the gear members of each pair of drive shafts.

13. The expandable spinal implant device of claim 12, wherein each body member includes an axially and circumferentially extending recess formed in a portion of the exterior surface thereof, the central body member being slidably received in the recess of each body member.

14. The expandable spinal implant device of claim 13 wherein, the first and second body members are axially displaceable relative to each other and the central body member, wherein the central body member is axially fixed relative to the first and second pairs of drive shafts, the first and second body members and the central body member being rotationally fixed by the first and second pairs of drive shafts, and wherein the central body member and the recesses extend around only a portion of the exterior surfaces of the first and second body members.

15. The expandable spinal implant device of claim 12, wherein the first and second body members each comprise a cylindrical shape defining the hollow interior extending from the first end to the second end thereof, wherein the first and second body members and the central body member are coaxially disposed about a central longitudinal axis, and wherein the first and second pair of drive shafts are positioned about sidewalls of the first and second body members radially outboard of the central longitudinal axis.

16. The expandable spinal implant device of claim 12, wherein the first and second pairs of drive shafts and associated gear members are cooperatively configured such that driving the one of the gear members of each pair of drive shafts simultaneously drives each pair of drive shafts to effect axial displacement of the first and second body members.

17. The expandable spinal implant device of claim 12, wherein the second ends of the first and second body members are spaced apart from and axially opposing each other, each of the central gear members being positioned between and axially spaced apart from the second ends of the body members when the implant device is in an unexpanded position and an expanded position and positions therebetween; and wherein the central body member includes a pair of attachment arms, the attachment arms coupled to one of the drive shafts of each pair of drive shafts adjacent the corresponding central gear members.

18. An expandable spinal implant device for supporting vertebral bodies comprising:

a first body member and a second body member each having first and second ends and defining a hollow interior, the first ends of each body member positionable toward a respective one of the vertebral bodies and including a convex portion extending therefrom;

a first pair of drive shafts and a second pair of drive shafts spaced apart from the first pair of drive shafts, the respective drive shafts of each pair of drive shafts having a central gear member rotationally coupling the respective shafts to each other, each pair of drive shafts threadably engaged at a first side to the first body member and at a second side to the second body member;

a central body member coupled to at least one shaft of the first and second pairs of drive shafts and configured to slidably engage an exterior surface of the first and second body members; and first and second articulating endplates moveably coupled to a respective convex portion, each articulating endplate including a bone engagement portion, a device engaging portion and a lock ring, the device engaging portion configured to pivot about one of the convex portions, the lock ring configured to selectively compress the device engaging portion against a surface of the convex portion in a desired position to secure the respective endplate to the respective body member in the desired position;

wherein the first and second pairs of drive shafts are operable to effect axial displacement of the first body member relative to the second body member by rotationally driving one of the gear members of each pair of drive shafts.

19. The expandable spinal implant of claim 18, further comprising an annular collar radially extending from a sidewall of each body member proximate the convex portion and a ring member rotationally coupled to the respective first and second body members adjacent the annular collar, each ring member being threadably coupled to a respective lock ring, wherein rotating the ring members draws the respective lock ring against the respective device engaging portion thereby compressing the device engaging portion against the respective convex portion to lock the respective articulating endplate in the desired position.

* * * * *